(12) United States Patent
Leyde et al.

(10) Patent No.: US 11,406,317 B2
(45) Date of Patent: Aug. 9, 2022

(54) METHOD FOR DETECTING NEUROLOGICAL AND CLINICAL MANIFESTATIONS OF A SEIZURE

(71) Applicant: LivaNova USA, Inc., Houston, TX (US)

(72) Inventors: Kent W. Leyde, Sammamish, WA (US); Michael Bland, Seattle, WA (US)

(73) Assignee: LivaNova USA, Inc., Houston, TX (US)

(*) Notice: Subject to any disclaimer, the term of this patent is extended or adjusted under 35 U.S.C. 154(b) by 799 days.

(21) Appl. No.: 14/630,867

(22) Filed: Feb. 25, 2015

(65) Prior Publication Data

US 2015/0164403 A1 Jun. 18, 2015

Related U.S. Application Data

(63) Continuation of application No. 12/343,376, filed on Dec. 23, 2008, now abandoned.

(60) Provisional application No. 61/017,501, filed on Dec. 28, 2007.

(51) Int. Cl.
*A61B 5/00* (2006.01)
*A61B 5/291* (2021.01)
*A61B 5/316* (2021.01)
*A61B 5/374* (2021.01)
(Continued)

(52) U.S. Cl.
CPC ............ *A61B 5/4094* (2013.01); *A61B 5/11* (2013.01); *A61B 5/291* (2021.01); *A61B 5/316* (2021.01); *A61B 5/374* (2021.01); *A61B 5/7221* (2013.01); *A61B 5/7246* (2013.01); *A61B 5/0031* (2013.01);
(Continued)

(58) Field of Classification Search
None
See application file for complete search history.

(56) References Cited

U.S. PATENT DOCUMENTS

| 3,218,638 A | 11/1965 | Honig |
| 3,498,287 A | 3/1970 | Ertl |
| 3,522,811 A | 8/1970 | Schwartz |

(Continued)

FOREIGN PATENT DOCUMENTS

| CA | 2251852 C | 4/1999 |
| CA | 2423840 C2 | 2/2002 |

(Continued)

OTHER PUBLICATIONS

Nijsen, T. M. E. et al; "The potential value of three-dimensional accelerometry for detection of motor seizures in severe epilepsy"; Epilepsy & Behavior 7 (2005) 74-84.*

(Continued)

*Primary Examiner* — Lori A. Clow
*Assistant Examiner* — Marie Archer
(74) *Attorney, Agent, or Firm* — Foley & Lardner LLP

(57) ABSTRACT

Methods for detecting neurological and clinical manifestations of a seizure are provided. Systems are described including a monitoring device having a communication assembly for receiving neurological data transmitted external to a patient from a transmitter implanted in a patient; a processor that processes the neurological data to estimate the patient's brain state; and an assembly for automatically recording clinical manifestation data in response to a brain state estimate by the processor.

17 Claims, 6 Drawing Sheets

(51) Int. Cl.
*A61B 5/11* (2006.01)
*A61N 1/36* (2006.01)

(52) U.S. Cl.
CPC ......... *A61B 5/7275* (2013.01); *A61N 1/36082* (2013.01)

(56) References Cited

U.S. PATENT DOCUMENTS

| | | |
|---|---|---|
| 3,575,162 A | 4/1971 | Gaarder |
| 3,837,331 A | 9/1974 | Ross |
| 3,850,161 A | 11/1974 | Liss |
| 3,863,625 A | 2/1975 | Viglione et al. |
| 3,882,850 A | 5/1975 | Bailin et al. |
| 3,918,461 A | 11/1975 | Cooper |
| 3,967,616 A | 7/1976 | Ross |
| 3,993,046 A | 11/1976 | Fernandez |
| 4,201,224 A | 5/1980 | John |
| 4,214,591 A | 7/1980 | Sato et al. |
| 4,279,258 A | 7/1981 | John |
| 4,305,402 A | 12/1981 | Katims |
| 4,334,545 A | 6/1982 | Shiga |
| 4,407,299 A | 10/1983 | Culver |
| 4,408,616 A | 10/1983 | Duffy et al. |
| 4,421,122 A | 12/1983 | Duffy |
| 4,471,786 A | 9/1984 | Inagaki |
| 4,494,950 A | 1/1985 | Fischell |
| 4,505,275 A | 3/1985 | Chen |
| 4,524,766 A | 6/1985 | Petersen |
| 4,545,388 A | 10/1985 | John |
| 4,566,061 A | 1/1986 | Ogden et al. |
| 4,566,464 A | 1/1986 | Piccone et al. |
| 4,573,481 A | 3/1986 | Bullara |
| 4,579,125 A | 4/1986 | Strob et al. |
| 4,590,946 A | 5/1986 | Loeb |
| 4,612,934 A | 9/1986 | Borkan |
| 4,679,144 A | 7/1987 | Cox et al. |
| 4,686,999 A | 8/1987 | Snyder et al. |
| 4,702,254 A | 10/1987 | Zabara |
| 4,735,208 A | 4/1988 | Wyler et al. |
| 4,768,176 A | 8/1988 | Kehr et al. |
| 4,768,177 A | 8/1988 | Kehr et al. |
| 4,785,827 A | 11/1988 | Fischer |
| 4,793,353 A | 12/1988 | Borkam |
| 4,817,628 A | 4/1989 | Zealear |
| 4,821,716 A | 4/1989 | Ghajar et al. |
| 4,838,272 A | 6/1989 | Lieber |
| 4,840,617 A | 6/1989 | Osterholm et al. |
| 4,844,075 A | 7/1989 | Liss et al. |
| 4,852,573 A | 8/1989 | Kennedy |
| 4,867,164 A | 9/1989 | Zabara |
| 4,873,981 A | 10/1989 | Abrams et al. |
| 4,878,498 A | 11/1989 | Abrams et al. |
| 4,903,702 A | 2/1990 | Putz |
| 4,920,979 A | 5/1990 | Bullara |
| 4,926,865 A | 5/1990 | Oman |
| 4,931,056 A | 6/1990 | Ghajar et al. |
| 4,934,372 A | 6/1990 | Corenman et al. |
| 4,955,380 A | 9/1990 | Edell |
| 4,978,680 A | 12/1990 | Sofia |
| 4,979,511 A | 12/1990 | Terry |
| 4,991,582 A | 2/1991 | Byers et al. |
| 4,998,881 A | 3/1991 | Lauks |
| 5,010,891 A | 4/1991 | Chamoun |
| 5,025,807 A | 6/1991 | Zabara |
| 5,026,376 A | 6/1991 | Greenberg |
| 5,031,618 A | 7/1991 | Mullett |
| 5,016,635 A | 12/1991 | Graupe |
| 5,070,873 A | 12/1991 | Graupe et al. |
| 5,082,861 A | 1/1992 | Sofia |
| 5,097,835 A | 3/1992 | Putz |
| RE34,015 E | 8/1992 | Duffy |
| 5,154,172 A | 10/1992 | Terry |
| 5,167,229 A | 12/1992 | Peckham et al. |
| 5,179,950 A | 1/1993 | Stainislaw |
| 5,181,520 A | 1/1993 | Wertheim et al. |
| 5,186,170 A | 2/1993 | Varichio |
| 5,188,104 A | 2/1993 | Wernicke |
| 5,190,029 A | 3/1993 | Bryon et al. |
| 5,193,539 A | 3/1993 | Schulman et al. |
| 5,193,540 A | 3/1993 | Schulman et al. |
| 5,205,285 A | 4/1993 | Baker, Jr. |
| 5,215,086 A | 6/1993 | Terry, Jr. et al. |
| 5,215,088 A | 6/1993 | Normann |
| 5,215,089 A | 6/1993 | Baker, Jr. |
| 5,222,494 A | 6/1993 | Baker, Jr. |
| 5,222,503 A | 6/1993 | Ives |
| 5,231,988 A | 8/1993 | Wernicke et al. |
| 5,235,980 A | 8/1993 | Varichio et al. |
| 5,237,991 A | 8/1993 | Baker, Jr |
| 5,251,634 A | 10/1993 | Weinberg |
| 5,263,480 A | 11/1993 | Wernicke et al. |
| 5,265,619 A | 11/1993 | Comby et al. |
| 5,269,302 A | 12/1993 | Swartz et al. |
| 5,269,303 A | 12/1993 | Wernicke et al. |
| 5,269,315 A | 12/1993 | Leuchter et al. |
| 5,292,772 A | 3/1994 | Sofia |
| 5,293,879 A | 3/1994 | Vonk |
| 5,299,118 A | 3/1994 | Martens et al. |
| 5,299,569 A | 4/1994 | Wernicke et al. |
| 5,300,094 A | 4/1994 | Kallok et al. |
| 5,304,206 A | 4/1994 | Baker, Jr. et al. |
| 5,311,876 A | 5/1994 | Olsen et al. |
| 5,312,439 A | 5/1994 | Loeb |
| 5,314,458 A | 5/1994 | Najafi et al. |
| 5,324,316 A | 6/1994 | Schulman et al. |
| 5,330,515 A | 7/1994 | Rutecki et al. |
| 5,335,657 A | 8/1994 | Terry et al. |
| 5,342,408 A | 8/1994 | deColriolis et al. |
| 5,342,409 A | 8/1994 | Mullett |
| 5,343,064 A | 8/1994 | Spangler et al. |
| 5,346,496 A | 9/1994 | Pennig |
| 5,349,962 A | 9/1994 | Lockard et al. |
| 5,351,394 A | 10/1994 | Weinberg |
| 5,361,760 A | 11/1994 | Normann |
| 5,365,939 A | 11/1994 | Ochs |
| 5,376,359 A | 12/1994 | Johnson |
| 5,392,788 A | 2/1995 | Hudspeth |
| 5,405,365 A | 4/1995 | Hoegnelid et al. |
| 5,405,367 A | 4/1995 | Schulman et al. |
| 5,411,540 A | 5/1995 | Edell et al. |
| 5,458,117 A | 10/1995 | Chamoun |
| 5,474,547 A | 12/1995 | Aebischer et al. |
| 5,476,494 A | 12/1995 | Edell et al. |
| 5,486,999 A | 1/1996 | Mebane |
| 5,513,649 A | 5/1996 | Gevins |
| 5,517,115 A | 5/1996 | Prammer |
| 5,531,778 A | 7/1996 | Maschino et al. |
| 5,540,730 A | 7/1996 | Terry, Jr. et al. |
| 5,540,734 A | 7/1996 | Zabara |
| 5,549,656 A | 8/1996 | Reiss |
| 5,555,191 A | 9/1996 | Hripcsak |
| 5,571,148 A | 11/1996 | Loeb et al. |
| 5,571,150 A | 11/1996 | Wernicke |
| 5,575,813 A | 11/1996 | Edell et al. |
| 5,578,036 A | 11/1996 | Stone et al. |
| 5,611,350 A | 3/1997 | John |
| 5,626,145 A | 5/1997 | Clapp et al. |
| 5,626,627 A | 5/1997 | Krystal et al. |
| 5,634,927 A | 6/1997 | Houston et al. |
| 5,638,826 A | 6/1997 | Wolpaw |
| 5,649,068 A | 7/1997 | Boser et al. |
| 5,672,154 A | 9/1997 | Sillen et al. |
| 5,683,422 A | 11/1997 | Rise |
| 5,683,432 A | 11/1997 | Goedeke et al. |
| 5,690,681 A | 11/1997 | Geddes et al. |
| 5,690,691 A | 11/1997 | Chen et al. |
| 5,697,369 A | 12/1997 | Long |
| 5,700,282 A | 12/1997 | Zabara |
| 5,704,352 A | 1/1998 | Tremblay et al. |
| 5,707,400 A | 1/1998 | Terry et al. |
| 5,711,316 A | 1/1998 | Elsberry et al. |
| 5,713,923 A | 2/1998 | Ward et al. |
| 5,715,821 A | 2/1998 | Faupel |
| 5,716,377 A | 2/1998 | Rise et al. |

(56) References Cited

U.S. PATENT DOCUMENTS

| | | |
|---|---|---|
| 5,720,294 A | 2/1998 | Skinner |
| 5,735,814 A | 4/1998 | Elsberry et al. |
| 5,743,860 A | 4/1998 | Hively et al. |
| 5,752,979 A | 5/1998 | Benabid |
| 5,769,778 A | 6/1998 | Abrams et al. |
| 5,776,434 A | 7/1998 | Purewal et al. |
| 5,782,798 A | 7/1998 | Rise |
| 5,782,874 A | 7/1998 | Loos |
| 5,782,891 A | 7/1998 | Hassler et al. |
| 5,792,186 A | 8/1998 | Rise |
| 5,800,474 A | 9/1998 | Bernabid et al. |
| 5,813,993 A | 9/1998 | Kaplan |
| 5,814,014 A | 9/1998 | Elsberry et al. |
| 5,815,413 A | 9/1998 | Hively et al. |
| 5,816,247 A | 10/1998 | Maynard |
| 5,824,021 A | 10/1998 | Rise |
| 5,832,932 A | 11/1998 | Elsberry et al. |
| 5,833,709 A | 11/1998 | Rise et al. |
| 5,857,978 A | 1/1999 | Hively et al. |
| 5,862,803 A | 1/1999 | Besson et al. |
| 5,876,424 A | 3/1999 | O'Phelan et al. |
| 5,899,922 A | 5/1999 | Loos |
| 5,913,881 A | 6/1999 | Benz et al. |
| 5,916,239 A | 6/1999 | Geddes et al. |
| 5,917,429 A | 6/1999 | Otis, Jr. et al. |
| 5,928,272 A | 7/1999 | Adkins |
| 5,931,791 A | 8/1999 | Saltzstein et al. |
| 5,935,128 A | 8/1999 | Carter et al. |
| 5,938,689 A | 8/1999 | Fischell et al. |
| 5,941,106 A | 8/1999 | Williamson et al. |
| 5,941,906 A | 8/1999 | Barreras et al. |
| 5,950,632 A | 9/1999 | Reber et al. |
| 5,954,687 A | 9/1999 | Baudino |
| 5,957,861 A | 9/1999 | Combs et al. |
| 5,971,594 A | 10/1999 | Sahai et al. |
| 5,975,085 A | 11/1999 | Rise |
| 5,978,702 A | 11/1999 | Ward et al. |
| 5,978,710 A | 11/1999 | Prutchi et al. |
| 5,995,868 A | 11/1999 | Dorfmeister et al. |
| 6,006,124 A | 12/1999 | Fischell et al. |
| 6,016,449 A | 1/2000 | Fischell et al. |
| 6,018,682 A | 1/2000 | Rise |
| 6,042,548 A | 3/2000 | Giuffre |
| 6,042,579 A | 3/2000 | Elsberry et al. |
| 6,051,017 A | 4/2000 | Loeb et al. |
| 6,052,619 A | 4/2000 | John |
| 6,061,593 A | 5/2000 | Fischell et al. |
| 6,066,142 A | 5/2000 | Serbousek et al. |
| 6,066,163 A | 5/2000 | John |
| 6,081,744 A | 6/2000 | Loos |
| 6,094,598 A | 7/2000 | Elsberry et al. |
| 6,109,269 A | 8/2000 | Rise et al. |
| 6,117,066 A | 9/2000 | Abrams et al. |
| 6,128,537 A | 10/2000 | Rise et al. |
| 6,128,538 A | 10/2000 | Fischell et al. |
| 6,134,474 A | 10/2000 | Fischell et al. |
| 6,161,045 A | 12/2000 | Fischell et al. |
| 6,167,304 A | 12/2000 | Loos |
| 6,171,239 B1 | 1/2001 | Humphrey |
| 6,176,242 B1 | 1/2001 | Rise |
| 6,205,359 B1 | 3/2001 | Boveja |
| 6,208,893 B1 | 3/2001 | Hofmann |
| 6,221,011 B1 | 4/2001 | Bardy |
| 6,227,203 B1 | 5/2001 | Rise et al. |
| 6,230,049 B1 | 5/2001 | Fischell et al. |
| 6,248,126 B1 | 6/2001 | Lesser et al. |
| 6,249,703 B1 | 6/2001 | Stanton |
| 6,263,237 B1 | 7/2001 | Rise |
| 6,280,198 B1 | 8/2001 | Calhoun et al. |
| 6,283,977 B1 | 9/2001 | Ericsson et al. |
| 6,304,775 B1 | 10/2001 | Iasemidis et al. |
| 6,309,406 B1 | 10/2001 | Jones et al. |
| 6,328,699 B1 | 12/2001 | Eigler |
| 6,337,997 B1 | 1/2002 | Rise |
| 6,339,725 B1 | 1/2002 | Naritoku |
| 6,341,236 B1 | 1/2002 | Osorio et al. |
| 6,343,226 B1 | 1/2002 | Sunde et al. |
| 6,353,754 B1 | 3/2002 | Fischell et al. |
| 6,354,299 B1 | 3/2002 | Fischell et al. |
| 6,356,784 B1 | 3/2002 | Lozano et al. |
| 6,356,788 B2 | 3/2002 | Boveja |
| 6,358,203 B2 | 3/2002 | Bardy |
| 6,358,281 B1 | 3/2002 | Berrang et al. |
| 6,360,122 B1 | 3/2002 | Fischell |
| 6,366,813 B1 | 4/2002 | DiLorenzo |
| 6,366,814 B1 | 4/2002 | Boveja |
| 6,374,140 B1 | 4/2002 | Rise |
| 6,386,882 B1 | 5/2002 | Linberg |
| 6,402,678 B1 | 6/2002 | Fischell et al. |
| 6,411,584 B2 | 6/2002 | Davis et al. |
| 6,411,854 B1 | 6/2002 | Tziviskos et al. |
| 6,427,086 B1 | 7/2002 | Fischell et al. |
| 6,434,419 B1 | 8/2002 | Gevins et al. |
| 6,442,421 B1 | 8/2002 | Le Van Quyen et al. |
| 6,443,891 B1 | 9/2002 | Grevious |
| 6,453,198 B1 | 9/2002 | Torgerson |
| 6,459,936 B2 | 10/2002 | Fischell |
| 6,463,328 B1 | 10/2002 | John |
| 6,466,822 B1 | 10/2002 | Pless |
| 6,471,645 B1 | 10/2002 | Warkentin et al. |
| 6,473,639 B1 | 10/2002 | Fischell et al. |
| 6,473,644 B1 | 10/2002 | Terry et al. |
| 6,480,743 B1 | 11/2002 | Kirkpatrick |
| 6,484,132 B1 | 11/2002 | Hively et al. |
| 6,488,617 B1 | 12/2002 | Katz |
| 6,496,724 B1 | 12/2002 | Levendowski et al. |
| 6,505,077 B1 | 1/2003 | Kast et al. |
| 6,510,340 B1 | 1/2003 | Jordan |
| 6,511,424 B1 | 1/2003 | Moore-Ede |
| 6,529,774 B1 | 3/2003 | Greene |
| 6,534,693 B2 | 3/2003 | Fischell et al. |
| 6,547,746 B1 | 4/2003 | Marino |
| 6,549,804 B1 | 4/2003 | Osorio et al. |
| 6,553,262 B1 | 4/2003 | Lang et al. |
| 6,560,473 B2 | 5/2003 | Dominguez |
| 6,560,486 B1 | 5/2003 | Osorio et al. |
| 6,571,123 B2 | 5/2003 | Ives et al. |
| 6,571,125 B2 | 5/2003 | Thompson |
| 6,572,528 B2 | 6/2003 | Rohan et al. |
| 6,587,719 B1 | 7/2003 | Barrett et al. |
| 6,591,132 B2 | 7/2003 | Gotman et al. |
| 6,591,137 B1 | 7/2003 | Fischell et al. |
| 6,591,138 B1 | 7/2003 | Fischell et al. |
| 6,594,524 B2 | 7/2003 | Estreller et al. |
| 6,597,953 B2 | 7/2003 | Boling |
| 6,597,954 B1 | 7/2003 | Pless et al. |
| 6,600,956 B2 | 7/2003 | Maschino |
| 6,606,521 B2 | 8/2003 | Paspa et al. |
| 6,609,020 B2 | 8/2003 | Gill |
| 6,609,025 B2 | 8/2003 | Barrett et al. |
| 6,618,623 B1 | 9/2003 | Pless et al. |
| 6,620,415 B2 | 9/2003 | Donovan |
| 6,622,036 B1 | 9/2003 | Suffin |
| 6,622,038 B2 | 9/2003 | Barrett et al. |
| 6,622,041 B2 | 9/2003 | Terry et al. |
| 6,622,047 B2 | 9/2003 | Barrett et al. |
| 6,647,296 B2 | 11/2003 | Fischell et al. |
| 6,650,779 B2 | 11/2003 | Vachtesvanos et al. |
| 6,658,287 B1 | 12/2003 | Litt et al. |
| 6,662,035 B2 | 12/2003 | Sochor |
| 6,665,562 B2 | 12/2003 | Gluckman et al. |
| 6,668,191 B1 | 12/2003 | Boveja |
| 6,671,555 B2 | 12/2003 | Gielen |
| 6,671,556 B2 | 12/2003 | Osorio |
| 6,678,548 B1 | 1/2004 | Echauz et al. |
| 6,684,105 B2 | 1/2004 | Cohen et al. |
| 6,687,538 B1 | 2/2004 | Hrdlicka et al. |
| 6,702,818 B2 | 3/2004 | Kupferschmid et al. |
| 6,735,467 B2 | 5/2004 | Wilson |
| 6,760,626 B1 | 7/2004 | Boveja |
| 6,768,969 B1 | 7/2004 | Nikitin et al. |
| 6,778,854 B2 | 8/2004 | Puskas |
| 6,782,292 B2 | 8/2004 | Whitehurst |
| 6,793,670 B2 | 9/2004 | Osorio |

(56) References Cited

U.S. PATENT DOCUMENTS

| | | |
|---|---|---|
| 6,810,285 B2 | 10/2004 | Pless et al. |
| 6,819,956 B2 | 11/2004 | DiLorenzo |
| 6,824,512 B2 | 11/2004 | Warkentin et al. |
| 6,873,872 B2 | 3/2005 | Gluckman et al. |
| 6,879,859 B1 | 4/2005 | Boveja |
| 6,893,395 B1 | 5/2005 | Kraus et al. |
| 6,901,294 B1 | 5/2005 | Whitehurst et al. |
| 6,901,296 B1 | 5/2005 | Whitehurst et al. |
| 6,904,390 B2 | 6/2005 | Nikitin et al. |
| 6,912,419 B2 | 6/2005 | Hill |
| 6,920,357 B2 | 7/2005 | Osorio |
| 6,921,538 B2 | 7/2005 | Donovan |
| 6,921,541 B2 | 7/2005 | Chasin et al. |
| 6,901,292 B2 | 8/2005 | Whitehurst |
| 6,923,784 B2 | 8/2005 | Stein |
| 6,931,274 B2 | 8/2005 | Williams |
| 6,934,580 B1 | 8/2005 | Osorio |
| 6,937,891 B2 | 8/2005 | Leinders et al. |
| 6,944,501 B1 | 9/2005 | Pless |
| 6,950,706 B2 | 9/2005 | Rodriquez |
| 6,973,342 B1 | 12/2005 | Swanson |
| 6,990,372 B2 | 1/2006 | Perron et al. |
| 7,010,351 B2 | 3/2006 | Firlik et al. |
| 7,033,326 B1 | 4/2006 | Pianca et al. |
| 7,089,059 B1 | 8/2006 | Pless |
| 7,137,969 B1 | 11/2006 | Mendez |
| 7,174,212 B1 | 2/2007 | Klehn et al. |
| 7,177,701 B1 | 2/2007 | Pianca |
| 7,212,851 B2 | 5/2007 | Donoghue et al. |
| 7,231,254 B2 | 6/2007 | DiLorenzo |
| 7,324,851 B1 | 1/2008 | DiLorenzo |
| 7,373,198 B2 | 5/2008 | Bibian et al. |
| 7,463,917 B2 | 12/2008 | Martinez |
| 7,631,015 B2 | 12/2009 | Gupta et al. |
| 7,805,196 B2 | 9/2010 | Miesel et al. |
| 7,881,798 B2 | 2/2011 | Miesel et al. |
| 8,055,348 B2 | 11/2011 | Heruth et al. |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0035338 A1 | 3/2002 | Dear et al. |
| 2002/0054694 A1 | 5/2002 | Vachtsevanos et al. |
| 2002/0072770 A1 | 6/2002 | Pless |
| 2002/0072776 A1 | 6/2002 | Osorio et al. |
| 2002/0072782 A1 | 6/2002 | Osorio et al. |
| 2002/0077670 A1 | 6/2002 | Archer et al. |
| 2002/0095099 A1 | 7/2002 | Quyen et al. |
| 2002/0099412 A1 | 7/2002 | Fischell et al. |
| 2002/0103512 A1 | 8/2002 | Echauz et al. |
| 2002/0109621 A1 | 8/2002 | Khair et al. |
| 2002/0111542 A1 | 8/2002 | Warkentin et al. |
| 2002/0116042 A1 | 8/2002 | Boling |
| 2002/0126036 A1 | 9/2002 | Flaherty et al. |
| 2002/0147388 A1 | 10/2002 | Mass et al. |
| 2002/0169485 A1 | 11/2002 | Press et al. |
| 2002/0177882 A1 | 11/2002 | DiLorenzo |
| 2002/0188330 A1 | 12/2002 | Gielen et al. |
| 2003/0004428 A1 | 1/2003 | Pless |
| 2003/0009207 A1 | 1/2003 | Paspa et al. |
| 2003/0013981 A1 | 1/2003 | Gevins et al. |
| 2003/0018367 A1 | 1/2003 | DiLorenzo |
| 2003/0028072 A1 | 2/2003 | Fischell et al. |
| 2003/0050549 A1 | 3/2003 | Sochor |
| 2003/0050730 A1 | 3/2003 | Greeven et al. |
| 2003/0073917 A1 | 4/2003 | Echauz et al. |
| 2003/0074033 A1 | 4/2003 | Pless et al. |
| 2003/0083716 A1 | 5/2003 | Nicolelis et al. |
| 2003/0114886 A1 | 6/2003 | Gluckman et al. |
| 2003/0144709 A1 | 7/2003 | Zabara et al. |
| 2003/0144711 A1 | 7/2003 | Pless et al. |
| 2003/0144829 A1 | 7/2003 | Geatz et al. |
| 2003/0149457 A1 | 8/2003 | Tcheng et al. |
| 2003/0158587 A1 | 8/2003 | Esteller et al. |
| 2003/0167078 A1 | 9/2003 | Weisner et al. |
| 2003/0174554 A1 | 9/2003 | Dunstone et al. |
| 2003/0176806 A1 | 9/2003 | Pineda et al. |
| 2003/0181955 A1 | 9/2003 | Gielen |
| 2003/0187621 A1 | 10/2003 | Nikitin et al. |
| 2003/0195574 A1 | 10/2003 | Osorio et al. |
| 2003/0195588 A1 | 10/2003 | Fischell et al. |
| 2003/0195602 A1 | 10/2003 | Boling |
| 2004/0034368 A1 | 2/2004 | Pless et al. |
| 2004/0039427 A1 | 2/2004 | Barrett et al. |
| 2004/0039981 A1 | 2/2004 | Riedl et al. |
| 2004/0039987 A1 | 2/2004 | Riedl et al. |
| 2004/0054297 A1 | 3/2004 | Wingeier et al. |
| 2004/0059761 A1 | 3/2004 | Hively |
| 2004/0068199 A1 | 4/2004 | Echauz et al. |
| 2004/0073273 A1 | 4/2004 | Gluckman et al. |
| 2004/0077995 A1 | 4/2004 | Ferek-Petric |
| 2004/0078160 A1 | 4/2004 | Frei et al. |
| 2004/0082984 A1 | 4/2004 | Osorio et al. |
| 2004/0087835 A1 | 5/2004 | Hively |
| 2004/0097802 A1 | 5/2004 | Cohen |
| 2004/0122281 A1 | 6/2004 | Fischell et al. |
| 2004/0122335 A1 | 6/2004 | Sackellares et al. |
| 2004/0127810 A1 | 7/2004 | Sackellares et al. |
| 2004/0133119 A1 | 7/2004 | Osorio et al. |
| 2004/0133248 A1 | 7/2004 | Frei et al. |
| 2004/0133390 A1 | 7/2004 | Osorio et al. |
| 2004/0138516 A1 | 7/2004 | Osorio et al. |
| 2004/0138517 A1 | 7/2004 | Osorio et al. |
| 2004/0138536 A1 | 7/2004 | Frei et al. |
| 2004/0138578 A1 | 7/2004 | Pineda et al. |
| 2004/0138579 A1 | 7/2004 | Deadwyler et al. |
| 2004/0138580 A1 | 7/2004 | Frei et al. |
| 2004/0138581 A1 | 7/2004 | Frei et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0147969 A1 | 7/2004 | Mann et al. |
| 2004/0152958 A1 | 8/2004 | Frei et al. |
| 2004/0153129 A1 | 8/2004 | Pless et al. |
| 2004/0158119 A1 | 8/2004 | Osorio et al. |
| 2004/0172089 A1 | 9/2004 | Whitehurst et al. |
| 2004/0176359 A1 | 9/2004 | Wermeling |
| 2004/0181263 A1 | 9/2004 | Balzer et al. |
| 2004/0199212 A1 | 10/2004 | Fischell |
| 2004/0210269 A1 | 10/2004 | Shalev et al. |
| 2004/0243146 A1 | 12/2004 | Chesbrough et al. |
| 2004/0267152 A1 | 12/2004 | Pineda et al. |
| 2005/0004621 A1 | 1/2005 | Boveja et al. |
| 2005/0010113 A1 | 1/2005 | Hall et al. |
| 2005/0010261 A1 | 1/2005 | Luders et al. |
| 2005/0015128 A1 | 1/2005 | Rezai et al. |
| 2005/0015129 A1 | 1/2005 | Mische |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021108 A1 | 1/2005 | Klosterman et al. |
| 2005/0021313 A1 | 1/2005 | Nititin et al. |
| 2005/0027328 A1 | 2/2005 | Greenstein |
| 2005/0033369 A1 | 2/2005 | Badelt |
| 2005/0043772 A1 | 2/2005 | Stahmann et al. |
| 2005/0043774 A1 | 2/2005 | Devlin et al. |
| 2005/0049649 A1 | 3/2005 | Luders et al. |
| 2005/0059867 A1 | 3/2005 | Cheng |
| 2005/0070810 A1 | 3/2005 | Kennedy |
| 2005/0070970 A1 | 3/2005 | Knudson et al. |
| 2005/0075067 A1 | 4/2005 | Lawson et al. |
| 2005/0075680 A1 | 4/2005 | Lowry et al. |
| 2005/0096710 A1 | 5/2005 | Kieval |
| 2005/0113885 A1 | 5/2005 | Haubrich et al. |
| 2005/0119703 A1 | 6/2005 | DiLorenzo |
| 2005/0124863 A1 | 6/2005 | Cook |
| 2005/0131493 A1 | 6/2005 | Boveja et al. |
| 2005/0137640 A1 | 6/2005 | Freeberg et al. |
| 2005/0143786 A1 | 6/2005 | Boveja |
| 2005/0143787 A1 | 6/2005 | Boveja et al. |
| 2005/0149123 A1 | 7/2005 | Lesser et al. |
| 2005/0182308 A1 | 8/2005 | Bardy |
| 2005/0182464 A1 | 8/2005 | Schulte et al. |
| 2005/0187789 A1 | 8/2005 | Hatlestad |
| 2005/0197590 A1 | 9/2005 | Osorio et al. |

(56) References Cited

U.S. PATENT DOCUMENTS

| | | |
|---|---|---|
| 2005/0203366 A1 | 9/2005 | Donoghue et al. |
| 2005/0203584 A1 | 9/2005 | Twetan et al. |
| 2005/0209218 A1 | 9/2005 | Meyerson et al. |
| 2005/0222503 A1 | 10/2005 | Dunlop et al. |
| 2005/0222626 A1 | 10/2005 | DiLorenzo |
| 2005/0222641 A1 | 10/2005 | Pless |
| 2005/0228249 A1 | 10/2005 | Boling |
| 2005/0228461 A1 | 10/2005 | Osorio et al. |
| 2005/0231374 A1 | 10/2005 | Diem et al. |
| 2005/0234355 A1 | 10/2005 | Rowlandson |
| 2005/0240245 A1 | 10/2005 | Bange et al. |
| 2005/0245970 A1 | 11/2005 | Erickson et al. |
| 2005/0245971 A1 | 11/2005 | Brockway et al. |
| 2005/0245984 A1 | 11/2005 | Singhal et al. |
| 2005/0266301 A1 | 12/2005 | Smith et al. |
| 2005/0277844 A1 | 12/2005 | Strother |
| 2006/0015034 A1 | 1/2006 | Martinerie et al. |
| 2006/0015153 A1 | 1/2006 | Gliner et al. |
| 2006/0094970 A1 | 5/2006 | Drew |
| 2006/0111644 A1 | 5/2006 | Guttag et al. |
| 2006/0122469 A1 | 6/2006 | Martel |
| 2006/0129056 A1 | 6/2006 | Leuthardt et al. |
| 2006/0142822 A1 | 6/2006 | Tulgar |
| 2006/0173259 A1 | 8/2006 | Flaherty et al. |
| 2006/0173510 A1 | 8/2006 | Besio et al. |
| 2006/0200038 A1 | 9/2006 | Savit et al. |
| 2006/0212092 A1 | 9/2006 | Pless et al. |
| 2006/0212093 A1 | 9/2006 | Pless et al. |
| 2006/0212096 A1 | 9/2006 | Stevenson |
| 2006/0217792 A1 | 9/2006 | Hussein et al. |
| 2006/0224191 A1 | 10/2006 | Dilorenzo |
| 2006/0235489 A1 | 10/2006 | Drew et al. |
| 2006/0253096 A1 | 11/2006 | Blakley et al. |
| 2006/0291968 A1 | 12/2006 | Greenberg |
| 2006/0293578 A1 | 12/2006 | Rennaker, II |
| 2006/0293720 A1 | 12/2006 | DiLorenzo et al. |
| 2007/0027367 A1 | 2/2007 | Oliver et al. |
| 2007/0027387 A1 | 2/2007 | Fendrock |
| 2007/0027514 A1 | 2/2007 | Gerber |
| 2007/0035910 A1 | 2/2007 | Stevenson |
| 2007/0043459 A1 | 2/2007 | Abbott, III et al. |
| 2007/0055320 A1 | 3/2007 | Weinand |
| 2007/0060973 A1 | 3/2007 | Ludvig et al. |
| 2007/0073355 A1 | 3/2007 | DiLorenzo |
| 2007/0073357 A1 | 3/2007 | Rooney et al. |
| 2007/0100398 A1 | 5/2007 | Sloan |
| 2007/0142862 A1 | 6/2007 | DiLorenzo |
| 2007/0149952 A1 | 6/2007 | Bland et al. |
| 2007/0150024 A1 | 6/2007 | Leyde et al. |
| 2007/0150025 A1 | 6/2007 | DiLorenzo |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0185890 A1 | 8/2007 | VanEpps et al. |
| 2007/0197878 A1 | 8/2007 | Shklarski |
| 2007/0213785 A1 | 8/2007 | Osorio et al. |
| 2007/0208212 A1 | 9/2007 | DiLorenzo |
| 2007/0213629 A1 | 9/2007 | Greene |
| 2007/0217121 A1 | 9/2007 | Fu et al. |
| 2007/0238939 A1* | 10/2007 | Giftakis ............... A61B 5/0402 600/301 |
| 2007/0244407 A1 | 10/2007 | Osorio |
| 2007/0250077 A1 | 10/2007 | Skakoon et al. |
| 2007/0250901 A1 | 10/2007 | McIntire et al. |
| 2007/0287931 A1 | 12/2007 | DiLorenzo |
| 2008/0021341 A1 | 1/2008 | Harris et al. |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0091090 A1 | 4/2008 | Guillory et al. |
| 2008/0103556 A1 | 5/2008 | Li et al. |
| 2008/0114417 A1 | 5/2008 | Leyde |
| 2008/0119900 A1 | 5/2008 | DiLorenzo |
| 2008/0161712 A1 | 7/2008 | Leyde |
| 2008/0161713 A1 | 7/2008 | Leyde et al. |
| 2008/0183096 A1 | 7/2008 | Snyder et al. |
| 2008/0183097 A1 | 7/2008 | Leyde et al. |
| 2008/0208074 A1 | 8/2008 | Snyder et al. |
| 2008/0221876 A1 | 9/2008 | Holdrich |
| 2008/0234598 A1 | 9/2008 | Snyder et al. |
| 2008/0255582 A1 | 10/2008 | Harris |
| 2008/0269630 A1* | 10/2008 | Denison ............... A61B 5/0478 600/544 |
| 2008/0273287 A1 | 11/2008 | Iyer et al. |
| 2009/0018609 A1 | 1/2009 | DiLorenzo |
| 2009/0062682 A1 | 3/2009 | Bland et al. |
| 2009/0062696 A1* | 3/2009 | Nathan ............... A61B 5/1107 600/595 |
| 2009/0137921 A1* | 5/2009 | Kramer ............... A61B 5/1118 600/544 |
| 2009/0171420 A1 | 7/2009 | Brown et al. |
| 2009/0264952 A1 | 10/2009 | Jassemidis et al. |
| 2010/0023089 A1 | 1/2010 | DiLorenzo |
| 2010/0030085 A1* | 2/2010 | Rojas Ojeda ........ A61B 5/0205 600/484 |
| 2010/0125219 A1 | 5/2010 | Harris et al. |
| 2010/0145176 A1 | 6/2010 | Himes |
| 2010/0168603 A1 | 7/2010 | Himes et al. |
| 2010/0168604 A1 | 7/2010 | Echauz et al. |
| 2010/0179627 A1 | 7/2010 | Floyd et al. |
| 2010/0217348 A1 | 8/2010 | Dilorenzo |
| 2010/0292602 A1 | 11/2010 | Worrell et al. |
| 2010/0302270 A1 | 12/2010 | Echauz et al. |
| 2011/0166430 A1 | 7/2011 | Harris et al. |
| 2011/0172554 A1 | 7/2011 | Leyde et al. |
| 2011/0201944 A1 | 8/2011 | Higgins et al. |
| 2011/0213222 A1 | 9/2011 | Leyde et al. |
| 2011/0218820 A1 | 9/2011 | Himes et al. |
| 2011/0219325 A1 | 9/2011 | Himes et al. |
| 2011/0230730 A1* | 9/2011 | Quigg ............... A61B 5/1121 600/301 |
| 2011/0260855 A1 | 10/2011 | John et al. |
| 2011/0319785 A1 | 12/2011 | Snyder et al. |
| 2014/0288620 A1 | 9/2014 | DiLorenzo |

FOREIGN PATENT DOCUMENTS

| | | |
|---|---|---|
| CA | 2428116 A1 | 5/2002 |
| CA | 2428383 A1 | 5/2002 |
| CA | 2425122 A1 | 6/2002 |
| CA | 2425004 A1 | 8/2002 |
| CA | 2456443 A1 | 1/2003 |
| CA | 2491987 A1 | 1/2004 |
| DE | 69832022 | 12/2005 |
| EP | 0124663 A1 | 11/1984 |
| EP | 0898460 B1 | 3/1999 |
| EP | 1017313 A4 | 7/2000 |
| EP | 1 107 693 | 6/2001 |
| EP | 1145735 A2 | 10/2001 |
| EP | 1145736 A2 | 10/2001 |
| EP | 1292900 A4 | 3/2003 |
| EP | 1307260 B1 | 5/2003 |
| EP | 1331967 A2 | 8/2003 |
| EP | 1335668 B1 | 8/2003 |
| EP | 1341580 A4 | 9/2003 |
| EP | 1404216 A2 | 4/2004 |
| EP | 1333753 A4 | 9/2004 |
| EP | 1525551 B1 | 4/2005 |
| EP | 1558121 A4 | 8/2005 |
| EP | 1558128 B1 | 8/2005 |
| EP | 1558130 A4 | 8/2005 |
| EP | 1558131 A4 | 8/2005 |
| EP | 1558132 B1 | 8/2005 |
| EP | 1558330 A4 | 8/2005 |
| EP | 1558334 A4 | 8/2005 |
| EP | 1562674 A4 | 8/2005 |
| EP | 0911061 B1 | 10/2005 |
| EP | 1609414 A2 | 12/2005 |
| EP | 1609414 a3 | 12/2005 |
| JP | 24033673 A2 | 2/2004 |
| SU | 1074484 A1 | 2/1984 |
| WO | WO 85/01213 A1 | 3/1985 |

(56) References Cited

FOREIGN PATENT DOCUMENTS

| WO | WO 92/00119 A1 | 1/1992 |
|---|---|---|
| WO | WO 97/26823 A1 | 7/1997 |
| WO | WO 97/34522 A1 | 9/1997 |
| WO | WO 97/34524 A1 | 9/1997 |
| WO | WO 97/34525 A1 | 9/1997 |
| WO | WO 97/39797 A1 | 10/1997 |
| WO | WO 97/42990 A1 | 11/1997 |
| WO | WO 97/45160 A1 | 12/1997 |
| WO | WO 98/49935 A1 | 11/1998 |
| WO | WO 99/20342 A1 | 4/1999 |
| WO | WO 99/56821 A1 | 11/1999 |
| WO | WO 99/56822 A1 | 11/1999 |
| WO | WO 00/07494 A2 | 2/2000 |
| WO | WO 00/10455 A1 | 3/2000 |
| WO | WO 01/41867 A1 | 6/2001 |
| WO | WO 01/48676 A1 | 7/2001 |
| WO | WO 01/49364 A1 | 7/2001 |
| WO | WO 01/67288 A2 | 9/2001 |
| WO | WO 01/75660 A1 | 10/2001 |
| WO | WO 02/09610 A1 | 2/2002 |
| WO | WO 02/09811 A1 | 2/2002 |
| WO | WO 02/36003 A1 | 5/2002 |
| WO | WO 02/38031 A2 | 5/2002 |
| WO | WO 02/38217 A2 | 5/2002 |
| WO | WO 02/49500 A2 | 6/2002 |
| WO | WO 02/058536 A2 | 8/2002 |
| WO | WO 02/067122 A1 | 8/2002 |
| WO | WO 03/001996 A2 | 1/2003 |
| WO | WO 03/009207 A1 | 1/2003 |
| WO | WO 03/030734 A2 | 4/2003 |
| WO | WO 03/035165 A1 | 5/2003 |
| WO | WO 03/084605 A1 | 10/2003 |
| WO | WO 04/008373 A2 | 1/2004 |
| WO | WO 04/032720 A2 | 4/2004 |
| WO | WO 04/034231 A2 | 4/2004 |
| WO | WO 04/034879 A2 | 4/2004 |
| WO | WO 04/034880 A2 | 4/2004 |
| WO | WO 04/034881 A2 | 4/2004 |
| WO | WO 04/034882 A2 | 4/2004 |
| WO | WO 04/034883 A2 | 4/2004 |
| WO | WO 04/034885 A2 | 4/2004 |
| WO | WO 04/034982 A2 | 4/2004 |
| WO | WO 04/034997 A2 | 4/2004 |
| WO | WO 04/034998 A2 | 4/2004 |
| WO | WO 04/035130 A2 | 4/2004 |
| WO | WO 04/36370 A2 | 4/2004 |
| WO | WO 04/36372 A2 | 4/2004 |
| WO | WO 04/36376 A2 | 4/2004 |
| WO | WO 04/36377 A2 | 4/2004 |
| WO | WO 04/37342 A2 | 5/2004 |
| WO | WO 04/43536 A1 | 5/2004 |
| WO | WO 04/091718 A2 | 10/2004 |
| WO | WO 05/007236 A2 | 1/2005 |
| WO | WO 05/028026 A1 | 3/2005 |
| WO | WO 05/028028 A1 | 3/2005 |
| WO | WO 05/031630 A2 | 4/2005 |
| WO | WO 05/051167 A1 | 6/2005 |
| WO | WO 05051306 A2 | 6/2005 |
| WO | WO 05/117693 A1 | 12/2005 |
| WO | WO 06/014971 A2 | 2/2006 |
| WO | WO 06/014972 A2 | 2/2006 |
| WO | WO-2007/150003 A2 | 12/2007 |

OTHER PUBLICATIONS

Cuppens, K. et al; "Detection of nocturnal epileptic seizures of pediatric patients using accelerometers: preliminary results"; IEEE Benelux EMBS Symposium; Dec. 6-7, 2007; p. 1-4.*

Nijsen, T. M.; "Detection of Subtle Nocturnal Motor Activity From 3-D Accelerometry Recording in Epilepsy Patients"; IEEE Transactions on Biomedical Engineering; vol. 54; No. 11; Nov. 2007; p. 2073-2081. (Year: 2007).*

Quensey, L. F.; "Clinical and EEG features of Complex Partial Seizures of Temporal Lobe Origin"; Epilepsia, 27 (Suppl. 2):S27-S45, 1986. (Year: 1986).*

D'Alessandro, M. et al; "A multi-feature and multi-channel univariate selection process for seizure prediction"; Clinical Neurophysiology, vol. 116, Issue 3, 2005, pp. 506-516. (Year: 2005).*

Osorio, I. et al; (2002), "Performance Reassessment of a Real-time Seizure-detection Algorithm on Long ECoG Series". Epilepsia, 43: 1522-1535. (Year: 2002).*

Reuber, Markus, et al. "Clinical significance of recurrent psychogenic nonepileptic seizure status." Journal of Neurology 250.11 (2003): 1355-1362. (Year: 2003).*

Adjouadi, et al. A new mathematical approach based on orthogonal operators for the detection of interictal spikes in epileptogenic data. Biomed. Sci. Instrum. 2004; 40: 175-80.

Adjouadi, et al. Detection of interictal spikes and artifactual data through orthogonal transformations. J. Clin. Neuorophysiol. 2005; 22(1):53-64.

Adjouadi, et al. Interictal spike detection using the Walsh transform. IEEE Trans. Biomed. Eng. 2004; 51(5):868-72.

Aksenova, et al. On-line disharmony detection for early prediction of epilepsy seizure onset. $5^{th}$ International Workshop Neural Coding 2003. Aulla (Italy) Sep. 20-25, 2003. (Abstract).

Aksevnova, et al. Nonparametric on-line detection of changes in signal spectral characteristics for early prediction of epilepsy seizure onset. J. Automation and Information Sciences. 2004; 36(8): 35-45.

Andrzejak, et al. Testing the null hypothesis of the nonexistence of a preseizure state. Physical Review E. 2003; 67: 010901-1-010901-4.

Andrzejak, et al. Bivariate surrogate techniques: necessity, strengths, and caveats. Physical Review E. 2003; 68: 066202-1-066202-15.

Aschenbrenner-Scheibe, et al. How well can epileptic seizures be predicted? An evaluation of a nonlinear method. Brain. 2003; 126: 2616-26.

Bangham et al. Diffusion of univalent ions across the lamellae of swollen phospholipids. 1965. J Mol. Biol. 13: 238-252.

Baruchi, et al. Functional holography of complex networks activity—From cultures to the human brain. Complexity. 2005; 10(3): 38 R 51.

Baruchi, et al. Functional holography of recorded neuronal networks activity. Neuroinformatics. 2004; 2(3): 333-51.

Ben-Hur, et al. Detecting stable clusters using principal component analysis. Methods Mol. Biol. 2003; 224: 159-82.

Bergey, et al. Epileptic seizures are characterized by changing signal complexity. Clin. Neurophysiol. 2001; 112(2): 241-9.

Betterton, et al. Determining State of Consciousness from the Intracranial Electroencephalogram (IEEG) for Seizure Prediction. From Proceeding (377) Modeling, Identification, and Control. 2003; 377-201: 313-317.

Bhattacharya, et al. Enhanced phase synchrony in the electroencephalograph gamma band for musicians while listing to music. Phys. Rev. E. 2001; 64:012902-1-4.

Boley, et al. Training Support Vector Machine using Adaptive Clustering. 2004 SIAM International Conference on Data Mining, Apr. 22-Apr. 24, 2004. Lake Buena Vista, FL, USA. 12 pages.

Burges, C. A Tutorial on Support Vector Machines for Pattern Recognition. Data Mining and Knowledge Discovery. 1998; 2: 121-167.

Cao, et al. Detecting dynamical changes in time series using the permutation entropy. Physical Review E. 2004; 70:046217-1-046217-7.

Carretero-Gonzalez, et al. Scaling and interleaving of subsystem Lyapunov exponents for spatio-temporal systems. Chaos. 1999; 9(2): 466-482.

Casdagli, et al. Characterizing nonlinearity in invasive EEG recordings from temporal lobe epilepsy. Physica D. 1996; 99 (2/3): 381-399.

Casdagli, et al. Nonlinear Analysis of Mesial Temporal Lobe Seizures Using a Surrogate Data Technique. Epilepsia. 1995; 36, suppl. 4, pp. 142.

Casdagli, et al. Non-linearity in invasive EEG recordings from patients with temporary lobe epilepsy. Electroencephalogr. Clin Neurophysiol. 1997; 102(2): 98-105.

(56) References Cited

OTHER PUBLICATIONS

Cerf, et al. Critically and synchrony of fluctuations in rhythmical brain activity: pretransitional effects in epileptic patients. Biol. Cybern. 2004; 90(4): 239-55.

Chaovalitwongse et al.; Reply to comments on "Performance of a seizure warning based on the dynamics of intracranial EEG"; Epilepsy Research, Elsevier Science Publishers, Amsterdam, NL; vol. 72; No. 1; pp. 82-84; Nov. 1, 2006.

Chaovalitwongse, et al. EEG Classification in Epilepsy. Annals. 2004; 2(37): 1-31.

Chaovalitwongse, et al. Performance of a seizure warning algorithm based on the dynamics of intracranial EEG. Epilepsy Res. 2005; 64(3): 93-113.

Chavez, et al. Spatio-temporal dynamics prior to neocortical seizures: amplitude versphase couplings. IEEE Trans. Biomed. Eng. 2003; 50(5):571-83.

Crichton, Michael, "Terminal Man", 1972, Ballantine Books, NY, NY, pp. 21-24, 32-33, 70-71, and 74-81.

D'Alessandro, et al. A multi-feature and multi-channel univariate selection process for seizure prediction. Clin. Neurophysiol. 2005; 116(3): 506-16.

D'Alessandro, et al. Epileptic seizure prediction using hybrid feature selection over multiple intracranial EEG electrode contacts: a report of four patients. IEEE Trans. Biomed. Eng. 2003; 50(5): 603-15.

Drury, et al. Seizure prediction using scalp electroencephalogram. Exp. Neurol. 2003; 184 Suppl 1: S9-18.

Ebersole, U.S. In search of seizure prediction: a critique. Clin. Neurophysiol. 2005; 116(3); 489-92.

Elbert et al. Chaos and Physiology: Deterministic Chaos in Excitable Cell Assemblies. Physiological Reviews. 1994; 74(1):1-47.

Elger, et al. Nonlinear EEG analysis and its potential role in epileptology. Epilepsia. 2000; 41 Suppl 3: S34-8.

Elger, et al. Seizure prediction by non-linear time series analysis of brain electrical activity. Eur. J. Neurosci. 1998; 10(2): 786-789.

Esteller, et al. A Comparison of Waveform Fractal Dimension Algorithms. IEEE Transactions on Circuits and Systems. 2001; vol. 48(2): 177-183.

Esteller, et al. Continuoenergy variation during the seizure cycle: towards an on-line accumulated energy. Clin. Neurophysiol. 2005; 116(3): 517-26.

Faul, et al. An evaluation of automated neonatal seizure detection methods. Clin. Neurophysiol. 2005; 116(7): 1533-41.

Fein, et al. Common reference coherence data are confounded by power and phase effects. Electroencephalogr. Clin. Neurophysiol. 1988; 69:581-584.

Fell, et al. Linear inverse filtering improves spatial separation of nonlinear brain dynamics: a simulation study. J. Neurosci. Methods. 2000; 98(1): 49-56.

Firpi, et al. Epileptic seizure detection by means of genetically programmed artificial features. GECCO 2005: Proceedings of the 2005 conference on Genetic and evolutionary computation, vol. 1, pp. 461-466, Washington DC, USA, 2005. ACM Press.

Fisher et al. 1999. Reassessment: Vagnerve stimulation for epilepsy, A report of the therapeutics and technology assessment subcommittee of the American Academy of Neurology. Neurology.53: 666-669.

Franaszczuk et al.; An autoregressive method for the measurement of synchronization of interictal and ictal EEG signals; Biological Cybernetics, vol. 81; No. 1; pp. 3-9; 1999.

Geva, et al. Forecasting generalized epileptic seizures from the EEG signal by wavelet analysis and dynamic unsupervised fuzzy clustering. IEEE Trans. Biomed. Eng. 1998; 45(10): 1205-16.

Gigola, et al. Prediction of epileptic seizures using accumulated energy in a multiresolution framework. J. Neurosci. Methods. 2004; 138(1-2): 107-111.

Guyon, I. An introduction to variable and feature selection. Journal of Machine Learning Research. 2003; 3:1157-1182.

Guyon, I. Multivariate Non-Linear Feature Selection with Kernel Multiplicative Updates and Gram-Schmidt Relief. BISC FLINT-CIBI 2003 Workshop. Berkeley. 2003; p. 1-11.

Harrison, et al. Accumulated energy revised. Clin. Neurophysiol. 2005; 116(3):527-31.

Harrison, et al. Correlation dimension and integral do not predict epileptic seizures. Chaos. 2005; 15(3): 33106-1-15.

Hearst M. Trends & Controversies: Support Vector Machines. IEEE Intelligent Systems. 1998; 13: 18-28.

Hively, et al. Channel-consistent forewarning of epileptic events from scalp EEG. IEEE Trans. Biomed. Eng. 2003; 50(5): 584-93.

Hively, et al. Detecting dynamical changes in nonlinear time series. Physics Letters A. 1999; 258: 103-114.

Hjorth, B. Source derivation simplifies topographical EEG interpretation. Am. J. EEG Technol. 1980; 20:121-132.

Huynh, J. A. Evaluation of Gene Selection Using Support Vector Machine Recursive Feature Elimination. Presentation slides. (41 pages) (May 26, 2004).

Huynh, J. A. Evaluation of Gene Selection Using Support Vector Machine Recursive Feature Elimination. Arizona State University. May 26, 2004. (28 pages).

Iasemidis, et al. Adaptive epileptic seizure prediction system. IEEE Trans. Biomed. Eng. 2003; 50(5):616-27.

Iasemidis, et al. Automated Seizure Prediction Paradigm. Epilepsia. 1998; vol. 39, pp. 56.

Iasemidis, et al. Chaos Theory and Epilepsy. The Neuroscientist. 1996; 2:118-126.

Iasemidis, et al. Comment on "Inability of Lyapunov exponents to predict epileptic seizures." Physical Review Letters. 2005; 94(1):019801-1.

Iasemidis, et al. Detection of the Preictal Transition State in Scalp-Sphenoidal EEG Recordings. American Clinical Neurophysiology Society Annual Meeting, Sep. 1996. pp. C206.

Iasemidis, et al. Dynamical Interaction of the Epileptogenic Focwith Extrafocal Sites in Temporal Lobe Epilepsy (TLE). Ann. Neurol. 1997; 42, pp. 429. pp. M146.

Iasemidis, et al. Epileptogenic FocLocalization by Dynamical Analysis of Interictal Periods of EEG in Patients with Temporal Lobe Epilepsy. Epilepsia. 1997; 38, suppl. 8, pp. 213.

Iasemidis, et al. Localizing Preictal Temporal Lobe Spike Foci Using Phase Space Analysis. Electroencephalography and Clinical Neurophysiology. 1990; 75, pp. S63-S64.

Iasemidis, et al. Long-term prospective on-line real-time seizure prediction. Clin. Neurophysiol. 2005; 116(3): 532-44.

Iasemidis, et al. Long-Time-Scale Temporo-spatial Patterns of Entertainment of Preictal Electrocorticographic Data in Human Temporal Lobe Epilepsy. Epilepsia. 1990; 31(5):621.

Iasemidis, et al. Measurement and Quantification of Spatio-Temporal Dynamics of Human Epileptic Seizures. In: Nonlinear Signal Processing in Medicine, Ed. M. Akay, IEEE Press. 1999; pp. 1-27.

Iasemidis, et al. Modelling of ECoG in temporal lobe epilepsy. Biomed. Sci. Instrum. 1988; 24: 187-93.

Iasemidis, et al. Nonlinear Dynamics of EcoG Data in Temporal Lobe Epilepsy. Electroencephalography and Clinical Neurophysiology. 1998; 5, pp. 339.

Iasemidis, et al. Phase space topography and the Lyapunov exponent of electrocorticograms in partial seizures. Brain Topogr. 1990; 2(3): 187-201.

Iasemidis, et al. Preictal Entrainment of a Critical Cortical Mass is a Necessary Condition for Seizure Occurrence. Epilepsia. 1996; 37, suppl. 5. pp. 90.

Iasemidis, et al. Preictal-Postictal Vers Postictal Analysis for Epileptogenic Foc Localization. J. Clin. Neurophysiol. 1997; 14, pp. 144.

Iasemidis, et al. Quadratic binary programming and dynamic system approach to determine the predictability of epileptic seizures. Journal of Combinatorial Optimization. 2001; 5: 9-26.

Iasemidis, et al. Quantification of Hidden Time Dependencies in the EEG within the Framework of Non-Linear Dynamics. World Scientific. 1993; pp. 30-47.

Iasemidis, et al. Spatiotemporal dynamics of human epileptic seizures. World Scientific. 1996; pp. 26-30.

(56) References Cited

OTHER PUBLICATIONS

Iasemidis, et al. Spatiotemporal Evolution of Dynamical Measures Precedes Onset of Mesial Temporal Lobe Seizures. Epilepsia. 1994; 358, pp. 133.
Iasemidis, et al. Spatiotemporal Transition to Epileptic Seizures: A Nonlinear Dynamical Analysis of Scalp and Intracranial EEG Recordings. (In Silva, F.L. Spatiotemporal Models in Biological and Artificial Systems. Ohmsha IOS Press. 1997; 37, pp. 81-88.).
Iasemidis, et al. The evolution with time of the spatial distribution of the largest Lyapunov exponent on the human epileptic cortex. World Scientific. 1991; pp. 49-82.
Iasemidis, et al. Time Dependencies in Partial Epilepsy. 1993; 34, pp. 130-131.
Iasemidis, et al. Time dependencies in the occurrences of epileptic seizures. Epilepsy Res. 1994; 17(1): 81-94.
Iasemidis, L. D. Epileptic seizure prediction and control. IEEE Trans. Biomed. Eng. 2003; 50(5):549-58.
Jerger, et al. Early seizure detection. Journal of Clin. Neurophysiol. 2001; 18(3):259-68.
Jerger, et al. Multivariate linear discrimination of seizures. Clin. Neurophysiol. 2005; 116(3):545-51.
Jouny, et al. Characterization of epileptic seizure dynamics using Gabor atom density. Clin. Neurophysiol. 2003; 114(3):426-37.
Jouny, et al. Signal complexity and synchrony of epileptic seizures: is there an identifiable preictal period? Clin. Neurophysiol. 2005; 116(3):552-8.
Kapiris, et al. Similarities in precursory features in seismic shocks and epileptic seizures. Europhys. Lett. 2005; 69(4);657-663.
Katz, et al. Does interictal spiking change prior to seizures? Electroencephalogr. Clin. Neurophysiol. 1991; 79(2):153-6.
Kerem, et al. Forecasting epilepsy from the heart rate signal. Med. Biol. Eng. Comput. 2005; 43(2):230-9.
Khalilov, et al. Epileptogenic actions of GABA and fast oscillations in the developing hippocampus. Neuron. 2005; 48(5):787-96.
Korn, et al. Is there chaos in the brain? II. Experimental evidence and related models. C. R. Biol. 2003; 326(9):787-840.
Kreuz, et al. Measure profile surrogates: a method to validate the performance of epileptic seizure prediction algorithms. Phys. Rev. E. 2004; 69(6 Pt 1):061915-1-9.
Lachaux, et al. Measuring phase synchrony in brain signals. Hum. Brain Mapp. 1999; 8(4):194-208.
Lai, et al. Controlled test for predictive power of Lyapunov exponents: their inability to predict epileptic seizures. Chaos. 2004; 14(3):630-42.
Lai, et al. Inability of Lyapunov exponents to predict epileptic seizures. Phys. Rev. Lett. 2003; 91(6):068102-1-4.
Latka, et al. Wavelet analysis of epileptic spikes. Phys. Rev. E. 2003; 67(5 Pt 1):052902 (6 pages).
Le Van Quyen, et al. Anticipating epileptic seizures in real time by a non-linear analysis of similarity between EEG recordings. Neuroreport. 1999; 10(10):2149-55.
Le Van Quyen, et al. Author's second reply. The Lancet. 2003; 361:971.
Le Van Quyen, et al. Comparison of Hilbert transform and wavelet methods for the analysis of neuronal synchrony. J. Neurosci. Methods. 2001; 111(2):83-98.
Le Van Quyen, et al. Nonlinear analyses of interictal EEG map the brain interdependences in human focal epilepsy. Physicia D. 1999; 127:250-266.
Le Van Quyen, et al. Preictal state identification by synchronization changes in long-term intracranial EEG recordings. Clin. Neurophysiol. 2005; 116(3):559-68.
Le Van Quyen, M. Anticipating epileptic seizures: from mathematics to clinical applications. C. R. Biol. 2005; 328(2):187-98.
Lehnertz, et al. Nonlinear EEG analysis in epilepsy: its possible use for interictal foe localization, seizure anticipation, and prevention. J. Clin. Neurophysiol. 2001; 18(3):209-22.
Lehnertz, et al. Seizure prediction by nonlinear EEG analysis. IEEE Eng. Med. Biol. Mag. 2003; 22(1):57-63.
Lehnertz, et al. The First International Collaborative Workshop on Seizure Prediction: summary and data description. Clin. Neurophysiol. 2005; 116(3):493-505.
Lehnertz, K. Non-linear time series analysis of intracranial EEG recordings in patients with epilepsy—and overview. Int. J. Psychophysiol. 1999; 34(1):45-52.
Lemos, et al. The weighted average reference montage. Electroencephalogr. Clin. Neurophysiol. 1991; 70(5):361-70.
Li, et al. Fractal spectral analysis of pre-epileptic seizures in terms of critically. J. Neural Eng. 2005; 2(2):11-16.
Li, et al. Linear and nonlinear measures and seizure anticipation in temporal lobe epilepsy. J. Comput. Neurosci. 2003; 15(3):335-45.
Li, et al. Non-linear, non-invasive method for seizure anticipation in focal epilepsy. Math. Biosci. 2003; 186(1):63-77.
Litt, et al. Prediction of epileptic seizures. Lancet Neurol. 2002; 1(1):22-30.
Litt, et al. Seizure prediction and the preseizure period. Curr. Opin. Neurol. 2002; 15(2):173-7.
Maiwald, et al. Comparison of three nonlinear seizure prediction methods by means of the seizure prediction characteristic. Physica D. 2004; 194:357-368.
Mangasarian, et al. Lagrangian Support Vector Machines. Journal of Machine Learning Research. 2001; 1:161-177.
Martinerie, et al. Epileptic seizures can be anticipated by non-linear analysis. Nat. Med. 1998; 4(10):1173-6.
McSharry, et al. Comparison of predictability of epileptic seizures by linear and a nonlinear method. IEEE Trans. Biomed. Eng. 2003; 50(5):628.33.
McSharry, et al. Linear and non-linear methods for automatic seizure detection in scalp electro-encephalogram recordings. Med. Biol. Eng. Comput. 2002; 40(4):447-61.
McSharry, P. E. Detection of dynamical transitions in biomedical signals using nonlinear methods. Lecture Notes in Computer Science 2004; 3215:483-490.
Meng, et al. Gaussian mixture models of ECoG signal features for improved detection of epileptic seizures. Med. Eng. Phys. 2004; 26(5):379-93.
Mizuno-Matsumoto, et al. Wavelet-crosscorrelation analysis can help predict whether bursts of pulse stimulation will terminate after discharges. Clin. Neurophysiol. 2002; 113(1):33-42.
Mormann et al.; Seizure prediction: the long and winding road; BRAIN; vol. 130; No. 2; pp. 314-333; Sep. 28, 2006.
Mormann, et al. Automated detection of a preseizure based on a decrease in synchronization in intracranial electroencephalogram recordings from epilepsy patients. Phys. Rev. E. 2003; 67(2 Pt 1):021912-1-10.
Mormann, et al. Epileptic seizures are preceded by a decrease in synchronization. Epilepsy Res. 2003; 53(3):173-85.
Mormann, et al. Mean phase coherence as a measure for phase synchronization and its application to the EEG of epilepsy patients. Physica D. 2000; 144:358-369.
Mormann, et al. On the predictability of epileptic seizures. Clin. Neurophysiol. 2005; 116(3):569-87.
Mormann, et al. Seizure anticipation: from algorithms to clinical practice. Curr. Opin. Neurol. 2006; 19(2):187-93.
Navarro, et al. Seizure anticipation in human neocortical partial epilepsy. Brain. 2002; 125:640-55.
Navarro, et al. Seizure anticipation: do mathematical measures correlate with video-EEG evaluation? Epilepsia. 2005; 46(3):385-96.
Niederhauser, et al. Detection of seizure precursors from depth-EEG using a sign periodogram transform. IEEE Trans. Biomed. Eng. 2003; 50(4):449-58.
Nigam, et al. A neural-network-based detection of epilepsy. Neurological Research. 2004; 26(1):55-60.
Osorio, et al. Automated seizure abatement in humans using electrical stimulation. Ann. Neurol. 2005; 57(2):258-68.
Osorio, et al. Performance reassessment of a real-time seizure-detection algorithm on long ECoG series. Epilepsia. 2002; 43(12):1522-35.
Osorio, et al. Real-time automated detection and quantitative analysis of seizures and short-term prediction of clinical onset. Epilepsia. 1998; 39(6):615-27.

(56) References Cited

OTHER PUBLICATIONS

Ossadtchi, et al. Hidden Markov modeling of spike propagation from interictal MEG data. Phys. Med. Biol. 2005; 50(14):3447-69.
Pflieger, et al. A noninvasive method for analysis of epileptogenic brain connectivity. Presented at the American Epilepsy Society 2004 Annual meeting, New Orleans. Dec. 6, 2004. Epilepsia. 2004; 45(Suppl. 7):70-71.
Platt, et al. Large Margin DAGs for Multiclass Classification. S.A. Solla. T.K. Leen and K.R. Muller (eds.). 2000; pp. 547-553.
Platt, J. C. Using Analytic QP and Sparseness to Speed Training of Support Vector Machines. Advances in Neural Information Processing Systems. 1999; 11:557-563.
Protopopescu, et al. Epileptic event forewarning from scalp EEG. J. Clin. Neurophysiol. 2001; 18(3):223-45.
Robinson, et al. Steady States and Global Dynamics of Electrical Activity in the Cerebral Coretex. Phys. Rev. E. 1998; (58):3557-3571.
Rothman et al.; Local Cooling: a therapy for intractable neocortical epilepsy; Epilepsy Currents; vol. 3; No. 5; pp. 153-156; Sep./Oct. 2003.
Rudrauf, et al. Frequency flows and the time-frequency dynamics of multivariate phase synchronization in brain signals. NeuroImage. 2005. (19 pages).
Saab, et al. A system to detect the onset of epileptic seizures in scalp EEG. Clin. Neurophysiol. 2005; 116:427-442.
Sackellares et al. Computer-Assisted Seizure Detection Based on Quantitative Dynamical Measures. American Electroencephalographic Society Annual Meeting, Sep. 1994.
Sackellares et al. Dynamical Studies of Human Hippocampin Limbic Epilepsy. Neurology. 1995; 45, Suppl. 4, pp. A 404.
Sackellares et al. Epileptic Seizures as Neural Resetting Mechanisms. Epilepsia. 1997; vol. 38, Sup. 3.
Sackellares et al. Measurement of Chaos to Localize Seizure Onset. Epilepsia. 1989; 30(5):663.
Sackellares et al. Predictability Analysis for an Automated Seizure Prediction algorrithim; Journal of Clinical Neurophysiology; vol. 23; No. 6; pp. 509-520; Dec. 2006.
Sackellares et al. Relationship Between Hippocampal Atrophy and Dynamical Measures of EEG in Depth Electrode Recordings. American Electroencephalographic Society Annual Meeting, Sep. 1995. pp. A105.
Sackellares, J. C. Epilepsy—when chaos fails. In: chaos in the brain? Eds. K. Lehnertz & C.E. Elger. World Scientific. 2000 (22 pages).
Salant, et al. Prediction of epileptic seizures from two-channel EEG. Med. Biol. Eng. Comput. 1998; 36(5):549-56.
Schelter et al.; Testing statistical significance of multivariate time series analysis techniques for epileptic seizure prediction; Chaos;: An Interdisciplinary Journal of Nonlinear Science; vol. 16; No. 013108; pp. 1-10; Jan. 2006.
Schelter, et al. Testing for directed influences among neural signals using partial directed coherence. J. Neurosci. Methods. 2006; 152-(1-2):210-9.
Schindler, et al. EEG analysis with simulated neuronal cell models helps to detect pre-seizure changes. Clin. Neurophysiol. 2002; 113(4):604-14.
Schwartzkroin, P. Origins of the Epileptic State. Epilepsia. 1997; 38, supply. 8, pp. 853-858.
Shoeb et al. Patient-specific seizure detection. MIT Computer Science and Artificial Intelligence Laboratory. 2004; pp. 193-194.
Snyder et al.; The statistics of a practical seizure warning system; Journal of Neural Engineering; vol. 5; pp. 392-401; 2008.
Staba, et al. Quantitative analysis of high-frequency oscillations (80-500 Hz) recorded in human epileptic hippocampand entorhinal cortex. J. Neurophysiol. 2002; 88(4): 1743-52.
Stefanski, et al. Using chaos synchronization to estimate the largest Lyapunov exponent of nonsmooth systems, discrete Dynamics in Nature and Society. 2000; 4:207-215.
Subasi, et al. Classification of EEG signals using neural network and logistic regression. Computer Methods Programs Biomed. 2005; 78(2):87-99.
Szoka et al. Procedure for preparation of liposomes with large internal aqueospace and high capture volume by reverse phase evaporation. 1978 Proc. Natl Acad. Sci. USA. 75:4194-4198.
Tass, et al. Detection of n: m Phase Locking from Noisy Data: Application to Magnetoencephalography. Physical Review Letters. 1998; 81(15):3291-3294.
Terry, et al. An improved algorithm for the detection of dynamical interdependence in bivariate time-series. Biol. Cybern. 2003; 88(2):129-36.
Tetzlaff, et al. Cellular neural networks (CNN) with linear weight functions for a prediction of epileptic seizures. Int'l. J. of Neural Systems. 2003; 13(6):489-498.
Theiler, et al. Testing for non-linearity in time series: the method of surrogate data. Physica D. 1992; 58:77-94.
Tsakalis, K. S. Prediction and control of epileptic seizures: Coupled oscillator models. Arizona State University. (Slide: 53 pages) (No date).
Van Drongelen, et al. Seizure anticipation in pediatric epilepsy: use of Kolmogorov entropy. Pediatr. Neurol. 2003; 29(3): 207-13.
Van Putten, M. Nearest neighbor phase synchronization as a measure to detect seizure activity from scalp EEG recordings. J. Clin. Neurophysiol. 2003; 20(5):320-5.
Venugopal, et al. A new approach towards predictability of epileptic seizures: KLT dimension. Biomed Sci. Instrum. 2003; 39:123-8.
Vonck, et al. Long-term amygdalohippocampal stimulation for refractory temporal lobe epilepsy. Ann. Neurol. 2002; 52(5):556-65.
Vonck, et al. Long-term deep brain stimulation for refractory temporal lobe epilepsy. Epilepsia. 2005; 46 (Suppl 5):98-9.
Vonck, et al. Neurostimulation for refractory epilepsy. Acta. Neurol. Belg. 2003; 103(4):213-7.
Weiss, P. Seizure prelude found by chaos calculation. Science News. 1998; 153(20):326.
Widman, et al. Reduced signal complexity of intracellular recordings: a precursor for epileptiform activity? Brain Res. 1999; 836(1-2):156-63.
Winterhalder, et al. The seizure prediction characteristic: a general framework to assess and compare seizure prediction methods. Epilepsy Behav. 2003; 4(3):318-25.
Wong et al.; A stochastic framework for evaluating seizure prediction algorithms using hidden markov models; Journal of Neurophysiology; vol. 97, No. 3; pp. 2525-2532; Oct. 4, 2006.
Yang et al.; Testing whether a prediction scheme is better than guess; Ch. 14 in Quantitative Neuroscience: Models, Algorithms, Diagnostics, and Therapeutic Applications; pp. 252-262; 2004.
Yang, et al. CLe Ver: A feature subset selection technique for multivariate time series. T.B. Ho, D. Cheung, and H. Liu (Eds.): PAKDD. 2005; LNAI 3518: 516-522.
Yang, et al. Relation between Responsiveness to Neurotransmitters and Complexity of Epileptiform Activity in Rat Hippocampal CA1 Neurons. Epilepsia. 2002; 43(11):1330-1336.
Yatsenko, et al. Geometric Models, Fiber Bundles, and Biomedical Applications. Proceedings of Institute of Mathematics of NAS of Ukraine. 2004; 50(Part 3):1518R1525.
Zaveri et al. Time-Frequency Analyses of Nonstationary Brain Signals. Electroencephalography and Clinical Neurophysiology. 1991; 79, pp. 28P-29P).
Zhang, et al. High-resolution EEG: cortical potential imaging of interictal spikes. Clin. Neurophysiol. 2003; 114(10):1963-73.
Ebersole, J.S. Functional neuroimaging with EEG source models to localize epileptogenic foci noninvasively. 2006. 3 pages.
Esteller, et al. Feature Parameter Optimization for Seizure Detection/Prediction. Proceedings of the 23rd Annual International Conference of the IEEE Engineering in Medicine and Biology Society, Istanbul, Turkey. Oct. 2001. 5 pages.
Gardner, A.B. A Novelty Detection Approach to Seizure Analysis from Intracranial EEG. Georgia Institute of Technology. Apr. 2004. 160 pages.
Hively, et al. Epileptic Seizure Forewarning by Nonlinear Techniques. ORNL/TM-2000/333 Oak Ridge National Laboratory. Nov. 2000. 41 pages.

(56) References Cited

OTHER PUBLICATIONS

Hoppe et al.; Accuracy of Patient Seizure Counts; Arch Neurol.;vol. 64; No. 11: pp. 1595-1599; 2007.
Hsu, et al. A practical guide to support vector classification. Technical report, Department of Computer Science and Information Technology, National Taiwan University, 2003. 12 pages.
Iasemidis, et al. The Use of Dynamical Analysis of EEG Frequency content in Seizure Prediction. American Electroencephalographic Society Annual Meeting. Oct. 1993. 2 pages.
Kraskov, A. Synchronization and Interdependence Measures and Their Applications to the Electroencephalogram of Epilepsy Patients and Clustering of Data. Feb. 2004. 106 pages.
Pittman, V. Flexible Drug Dosing Procedures Less Side-effects in People With Epilepsy. Dec. 29, 2005. 3 pages.
Rahimi, et al. On the Effectiveness of Aluminum Foil Helmets: An Empirical Study. Feb. 17, 2005. 5 pages.
Remington, et al. Remington's Pharmaceutical Sciences, Mack Publishing co., Easton PA. 1990. pp. 674-677 and 1072-1081.
Sheridan, T. Humans and Automation: System Design and Research Issues. NY: John Wiley. 2002. 144 pages.
Wells, R. B. Spatio-Temporal Binding and Dynamic Cortical Organization: Research Issues. Mar. 2005. 68 pages.
Winterhalder, et al. Sensitivity and specificity of coherence and phase synchronization analysis. 2006. 9 pages.
Yang, et al. A supervised feature subset selection technique for multivariate time series. 2005. 10 pages.
Tsakalis, K.S. Prediction and control of epileptic seizures: Coupled oscillator models. Arizona State University. (Slide: 53 pages) (2005).

\* cited by examiner

| | Prediction algorithm output - Detection algorithm output | | | |
|---|---|---|---|---|
| Safety algorithm output | 0 0 | 0 1 | 1 1 | 1 0 |
| 0 | Unknown "Yellow" | Seizure detected "Red flashing" | Seizure detected "Red flashing" | Seizure predicted "Red blinking" |
| 1 | Safe "Green" | Seizure detected "Red flashing" | Seizure detected "Red flashing" | Seizure predicted "Red blinking" |

FIG. 4

METHOD FOR DETECTING NEUROLOGICAL AND CLINICAL MANIFESTATIONS OF A SEIZURE

CROSS-REFERENCE TO RELATED APPLICATIONS

This application is a continuation of U.S. patent application Ser. No. 12/343,376 filed Dec. 23, 2008, which claims the benefit of priority from U.S. Provisional Application No. 61/017,501, filed Dec. 28, 2007, both of which are incorporated by reference herein in their entirety.

INCORPORATION BY REFERENCE

All publications, patents, and patent applications mentioned in this specification are herein incorporated by reference to the same extent as if each individual publication or patent application was specifically and individually indicated to be incorporated by reference.

BACKGROUND OF THE INVENTION

Systems have been proposed that can monitor neurological data from a patient and use the data to detect a neurological event, such as the onset of an epileptic seizure. In such systems it may be desirable to additionally monitor a patient's notes and seizure logs to derive or change device settings.

Seizure logs, both written and electronic, have been used to monitor patient's seizure activity. However, conventional electronic seizure logs require the user, patient, or clinician, to take action to enter information into the seizure log. Examples of electronic seizure logs that require user activation are described in U.S. patent application Ser. No. 11/436,190 (US 2006/0212092), filed May 16, 2006, and U.S. patent application Ser. No. 11/412,230, filed Apr. 26, 2006 (US 2006/0235489), the disclosures of which are incorporated by reference herein in their entireties. However, as described in "Accuracy of Patient Seizure Counts," Christian Hoppe, PhD; Annkathrin Poepel, MD; Christian E. Elger, PhD, MD, Arch Neurol. 2007; 64(11):1595-1599, patient driven seizure logs are notoriously inaccurate, and provide only marginally useful data to both the physician and patient, and if used to derive new device settings may in fact detrimentally effect device performance. Additionally, clinical seizure activity that is monitored and/or recorded while the patient is in a hospital or other non-ambulatory setting requires the patient to be restricted to a confined location before the clinical manifestation data can be monitored and/or recorded. This prevents the patient from going about daily activities.

It would be beneficial to have a system that can automatically acquire data indicative of the occurrence of a clinical seizure without user intervention. It would also be beneficial to have a system wherein the acquisition of data indicative of the occurrence of a clinical seizure may be associated with the system's performance, and thereafter used to improve the performance of the system. It would additionally be beneficial to have an ambulatory system that can monitor and/or record data that is indicative of a clinical manifestation of a seizure without user intervention.

SUMMARY OF THE INVENTION

One aspect of the invention provides a method of comparing a patient's neurological data to data that is indicative of the patient's clinical manifestation of a seizure. In some embodiments, the method includes the steps of monitoring neurological data from a patient indicative of the patient's propensity for having a seizure; automatically recording clinical manifestation data from the patient that may be indicative of the occurrence of a clinical seizure; and analyzing the automatically recorded clinical manifestation data and the monitored neurological data to determine if one of the clinical manifestation data and the neurological data indicates the occurrence of a seizure while the other does not.

In some embodiments, the neurological data is EEG data, and the method includes the step of determining the patient's brain state based on the EEG data. The step of analyzing the clinical manifestation data with the neurological data may include the step of comparing the clinical manifestation data with the brain state to determine if one of the clinical manifestation data and the brain state indicates the occurrence of a seizure while the other does not. The step of determining the brain state may include the step of determining if the patient is in at least one of a pro-ictal state and an ictal state, and the step of automatically monitoring clinical manifestation data may include the step of automatically recording clinical manifestation data when the patient enters the pro-ictal or the ictal state. The method may also include the step of retraining an algorithm used in determining the patient's brain state if the determined brain state indicates seizure activity and the clinical manifestation data does not.

In some embodiments, the step of automatically monitoring clinical manifestation data includes the step of substantially continuously buffering clinical manifestation data during monitoring of neurological data from the patient. The method may also include the step of determining the patient's brain state based on the neurological data, and further comprising permanently storing in memory the monitored clinical manifestation data when the brain state indicates at least an increased likelihood of having a seizure.

In some embodiments, the step of automatically recording clinical manifestation data from the patient includes the step of annotating the monitored neurological data from a patient with an indication of the occurrence of the clinical manifestation of the seizure. The neurological data may be, e.g., an EEG recording, and annotating the neurological data may include the step of annotating the EEG data with an indication of the occurrence of the clinical manifestation of the seizure.

In some embodiments, the step of automatically recording clinical manifestation data includes the step of automatically recording convulsion activity in the patient. In other embodiments, the step of automatically recording clinical manifestation data includes the step of automatically recording audio of the patient. In still other embodiments, the step of automatically recording clinical manifestation data includes the step of automatically recording heart rate signals of the patient.

In some embodiments, the step of automatically recording clinical manifestation data includes the step of automatically recording video of the patient. In other embodiments, the method includes the step of transmitting in substantially real-time the neurological data from an implanted device to an external device, wherein automatically monitoring clinical manifestation data is performed by the external device when the step of monitoring the neurological data indicates a change from a first brain state to a second brain state. The step of automatically recording clinical manifestation data may include the step of recording clinical manifestation data in response to the occurrence of an event in the patient's condition. In some embodiments, the method is performed with an ambulatory patient monitoring device.

Another aspect of the invention provides a method of comparing a patient's estimated brain state to data that is indicative of clinical manifestation of a seizure. In some embodiments, the method includes the step of monitoring neurological data (such as, e.g., EEG data) from a patient; determining the patient's brain state based on the monitored neurological data, wherein the brain state indicates the patient's propensity for having a seizure; monitoring clinical manifestation data from the patient that is indicative of the occurrence of a clinical seizure; and comparing the monitored clinical manifestation data with the patient's determined brain state to determine if the brain state indicates the occurrence of a seizure while the clinical manifestation data does not. In some embodiments, the monitoring step is performed automatically, such as, e.g., in response to an occurrence of an event in the patient's condition. The method may be performed by an ambulatory patient monitoring device.

In some embodiments, the step of determining the brain state includes the step of determining if the patient is in at least one of a pro-ictal state and an ictal state or in at least one of a contra-ictal state, a pro-ictal state, and an ictal state. The method may also include the step of recording clinical manifestation data when the patient enters the pro-ictal or the ictal state. In some embodiments, the method includes the step of retraining an algorithm used in determining the patient's brain state if the determined brain state indicates seizure activity and the clinical manifestation data does not.

In some embodiments, the step of monitoring clinical manifestation data includes the step of substantially continuously buffering clinical manifestation data during monitoring of neurological data from the patient. The method may also include the step of permanently storing in memory the monitored clinical manifestation data when the brain state indicates at least an increased likelihood of having a seizure.

In some embodiments, the step of recording clinical manifestation data from the patient includes the step of annotating the monitored neurological data from a patient with an indication of the occurrence of the clinical manifestation of the seizure. In embodiments in which the neurological data includes an EEG recording, the step of annotating the neurological data may include the step of annotating the EEG data with an indication of the occurrence of the clinical manifestation of the seizure.

In various embodiments of the method, the step of recording clinical manifestation data may include recording convulsion activity in the patient, recording audio of the patient, recording heart rate signals of the patient, and/or recording video of the patient. The method may also include the step of transmitting in substantially real-time the neurological data from an implanted device to an external device, wherein monitoring clinical manifestation data is performed by the external device when monitoring the neurological data indicates a change from a first brain state to a second brain state.

Yet another aspect of the invention provides a method of automatically recording clinical manifestation data from a patient. In some embodiments, the method includes the steps of monitoring neurological data from a patient; estimating the patient's brain state based on the monitored neurological data; determining a change in the patient's brain state; and automatically recording clinical manifestation data from the patient using a device worn or held by the patient.

In some embodiments, clinical manifestation data is recorded when one or more specified changes in brain state occurs. In some embodiments, the step of determining a change in the patient's brain state includes the step of determining that the patient has entered into either a pro-ictal state or an ictal state or that the patient has gone from a contra-ictal state to a pro-ictal state or from a pro-ictal state to an ictal state. In some embodiments, the method includes the step of comparing either the neurological data or the brain state with the recorded clinical manifestation data to determine if one of the clinical manifestation data and the neurological data or brain state indicates the occurrence of a seizure while the other does not.

Still another aspect of the invention provides a monitoring device having a communication assembly for receiving neurological data transmitted external to a patient from a transmitter implanted in a patient; a processor that processes the neurological data to estimate the patient's brain state; and an assembly for automatically recording clinical manifestation data in response to a brain state estimate by the processor. In some embodiments, the assembly for automatically recording clinical manifestation data includes a data buffer configured to continuously buffer clinical manifestation data during monitoring of neurological data from the patient. Some embodiments of the invention also include an annotator configured to annotate monitored neurological data with an indication of the occurrence of clinical manifestation of a seizure.

In some embodiments, the assembly for automatically recording clinical manifestation data includes a convulsion detector, an audio input device, a heart rate detector, and/or a video camera. In some embodiments, monitoring device is adapted to be carried by an ambulatory patient.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4 is a schematic diagram showing other further aspects of a monitoring system according to an embodiment of the invention.

DETAILED DESCRIPTION OF THE INVENTION

Figure 1:
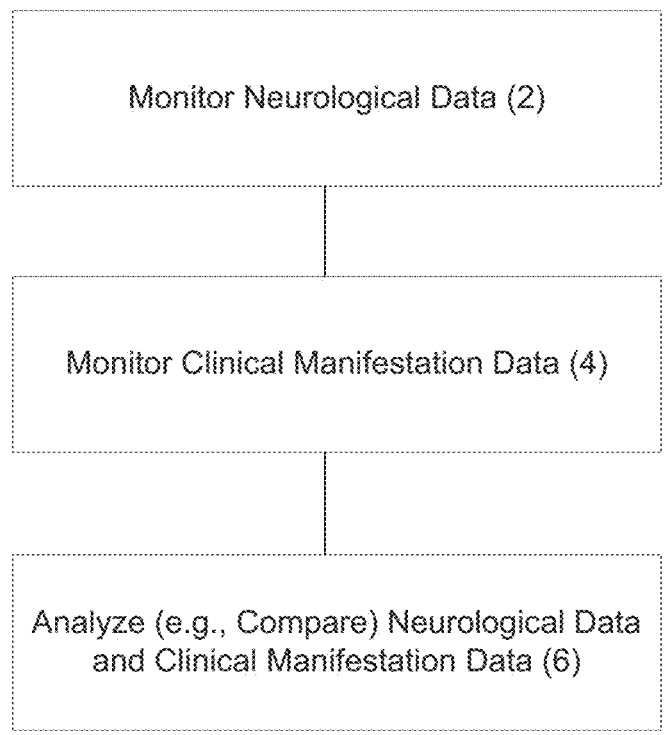
FIG. 1 is a flow chart showing an embodiment of the invention.

Described herein are systems and methods for determining if an observable clinical manifestation of a seizure is associated with the system's detection of a seizure or the system's determination of a patient's increased propensity for having a seizure (also referred to herein as "seizure prediction"). The system generally monitors a physiological signal (e.g., neurological data such as an electroencephalogram, or EEG) from the patient to detect the occurrence of a seizure and/or to estimate the patient's propensity for having a seizure. The correlation between observable clinical manifestation data of a seizure and the system's detection of a seizure and/or estimation of the patient's propensity for the seizure can assist in determining if the system is accurately estimating the propensity for having a seizure (or the detection of the seizure). The occurrence of an observable clinical manifestation of a seizure without the system's estimation of an increased propensity for the seizure or detection of a seizure suggests the system "missed" the seizure (i.e., a false negative), while the system's estimation of an increased propensity for a seizure or detection of a seizure without an observable clinical manifestation of a seizure may suggest a false positive or the detection or prediction of a sub-clinical seizure (i.e., an electrographic seizure that does not manifest clinically). Thus, the correlation between the two can be used to train the system (e.g., train an algorithm) to increase the accuracy of the system's estimation of the patient's propensity for a seizure and/or the system's detection capabilities. The correlation between the two can also help to create a system that is enabled with patient-specific algorithms (e.g., safety algorithm, prediction algorithm, detection algorithm).

The term "condition" as used herein refers generally to the patient's underlying disease or disorder—such as epilepsy, depression, Parkinson's disease, headache disorder, dementia, etc. The term "state" is used herein to generally refer to calculation results or indices that are reflective of a categorical approximation of a point (or group of points) along a single or multi-variable state space continuum. The estimation of the patient's state does not necessarily constitute a complete or comprehensive accounting of the patient's total situation. State typically refers to the patient's state within their neurological condition.

For example, for a patient suffering from epilepsy, at any point in time the patient may be in a different state along the continuum, such as an ictal state (a state in which a neurological event, such as a seizure, is occurring), a pre-ictal state (a state that immediately precedes the ictal state), a pro-ictal state (a state in which the patient has an increased risk of transitioning to the ictal state), an inter-ictal state (a state in between ictal states), a contra-ictal state (a protected state in which the patient has a low risk of transitioning to an ictal state within a calculated or predetermined time period), or the like. A pro-ictal state may transition to either an ictal or inter-ictal state. A pro-ictal state that transitions to an ictal state may also be referred to herein as a "pre-ictal state." The systems described herein may be adapted to be able to determine if the patient is in any or all of the above "states." Thus, the systems described herein may include systems designed to simply detect a seizure (i.e., to detect that the patient has entered an ictal state) as well as systems that are adapted to detect when the patient changes between at least two of the above described states. In addition, some systems may detect more than the states described herein.

The estimation and characterization of "state" may be based on one or more patient-dependent parameters from the a portion of the patient's body, such as neurological data from the brain, including but not limited to electroencephalogram signals "EEG" and electrocorticogram signals "ECoG" or intracranial EEG (referred to herein collectively as EEG"), brain temperature, blood flow in the brain, concentration of AEDs in the brain or blood, etc.). While parameters that are extracted from brain-based signals are preferred, the system may also extract parameters from other physiological signals of the body, such as heart rate, respiratory rate, chemical concentrations, etc.

An "event" is used herein to refer to a specific event, or change, in the patient's condition. Examples of such events include transition from one state to another state, e.g., an electrographic onset of seizure, an end of seizure, or the like. For conditions other than epilepsy, the event could be an onset of a migraine headache, a convulsion, or the like.

The occurrence of a seizure may be referred to as a number of different things. For example, when a seizure occurs, the patient is considered to have exited a "pre-ictal state" or "pro-ictal state" and has transitioned into the "ictal state". However, the clinical onset of a seizure is described herein to be a separate event from the electrographic onset of a seizure, but both may of course be occurring at the same time. The clinical onset of a seizure includes all clinical manifestations of a seizure. Clinical manifestations of a seizure, as used herein, includes an aura, a rhythmic jerking, stiffening or shaking of one or more limbs (referred to herein as "convulsion"), an ictal-moan, or any other commonly known clinical manifestation of a seizure, including any combination thereof.

A patient's "propensity" for a seizure is a measure of the likelihood of transitioning into the ictal state. The patient's propensity for seizure may be estimated by determining which "state" the patient is currently in. As noted above, the patient is deemed to have an increased propensity for transitioning into the ictal state (e.g., have a seizure) when the patient is determined to be in a pro-ictal state. Likewise, the patient may be deemed to have a low propensity for transitioning into the ictal state for a time period when it is determined that the patient is in a contra-ictal state. As stated above, the systems do not necessarily need to be able to determine the patient's propensity for a seizure, but can simply detect the occurrence of a seizure.

One exemplary simplified method is shown in FIG. 1. The method comprises monitoring neurological data from a patient (e.g., EEG data) which is indicative of the patient's propensity for having a seizure (2). The method also includes monitoring clinical manifestation data from the patient that is indicative of the occurrence of a clinical seizure (4). Next, the method includes analyzing (e.g., comparing) the monitored clinical manifestation data and the neurological data to determine if one of the clinical manifestation data and the neurological data indicates the occurrence of a seizure while the other does not (6).

As used herein, "clinical manifestation data" may include any one or a combination of audio data (e.g., recording of an ictal moan), video data of the patient, data from an accelerometer provided on or in the patient's body (e.g., attached externally to or implanted in a patient's limb so as to record jerky rhythmic movements indicative of the patient's clinical seizure type), data from a heart rate monitor (e.g., to detect changes in heart rate, tachycardia, bradycardia, etc.), or data from other physiological or non-physiological sensors that are indicative of an occurrence of a seizure. While the remaining discussion highlights recording audio data, other types of clinical manifestation data may also be recorded.

Figure 2:
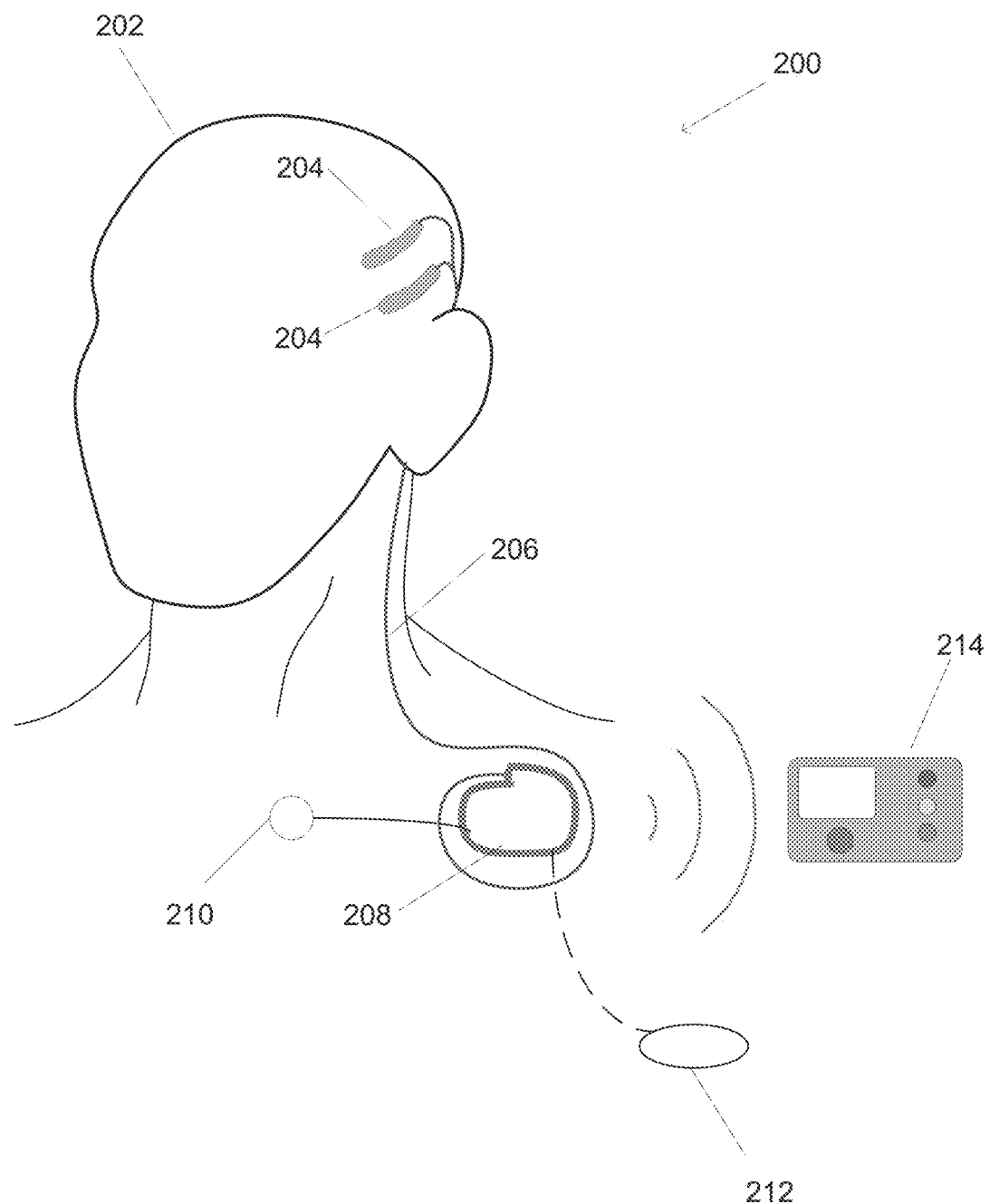
FIG. 2 shows an embodiment of an ambulatory monitoring system according to an embodiment of the invention.

FIG. 2 illustrates an exemplary simplified system that may be used to monitor a patient's neurological data and monitor clinical manifestation data from the patient. The system can also determine the patient's brain state based on the monitored neurological data.

The system 200 as shown comprises one or more electrodes 204 configured to measure neurological signals from patient 202. Electrodes 204 may be located anywhere in or on the patient. In this embodiment, electrodes 204 are configured in one or more arrays and are positioned to sample electrical activity from the patient's brain. Electrodes 204 may be attached to the surface of the patient's body (e.g., scalp electrodes), attached to or positioned adjacent the skull (e.g., subcutaneous electrodes, bone screw electrodes, sphenoidal electrodes, and the like), or may be implanted intracranially in patient 202. The electrode arrays include one or more macroelectrodes that are configured to monitor groups of neurons, or one or more microelectrodes that are configured to monitor a single neuron. In one embodiment, one or more of electrodes 204 will be implanted adjacent a previously identified epileptic focus, a portion of the brain where such a focus is believed to be located, or adjacent a portion of a seizure network.

Any number of electrodes 204 may be used, but electrodes 204 will preferably include between 1 electrode and 24 electrodes, and preferably between about 4 electrodes and 16 electrodes. The electrodes may take a variety of forms. The electrodes can comprise grid electrodes, strip electrodes and/or depth electrodes which may be permanently implanted through burr holes in the head.

In addition to measuring brain activity, other sensors may be employed to measure other physiological signals or non-physiological signals from patient 202 either for monitoring the patient's condition or to measure clinical manifestation data. For example, the system can include one or more of heart monitor 210 and accelerometer 212 that can be used to monitor data from the patient that is indicative of a seizure, or they can be used to monitor clinical manifestation data (e.g., heart rate and convulsion data, respectively) as described herein.

In an embodiment, electrodes 204 will be configured to substantially continuously sample the brain activity in the immediate vicinity of electrodes 204. Electrodes 204 are shown electrically joined via leads 206 to implanted device 208, but could be wirelessly coupled to implanted device 208 or other external device as is more fully described in the minimally invasive monitoring systems described in co-pending application Ser. No. 11/766,742, filed Jun. 21, 2007, the disclosure of which is incorporated herein by reference. In one embodiment, leads 206 and implanted device 208 are implanted inside patient 202. For example, the implanted device 208 may be implanted in a sub-clavicular cavity or abdominal cavity of patient. In alternative embodiments, the leads 206 and implanted device 208 may be implanted in other portions of the patient's body (e.g., in the head) or attached to the patient 202 externally.

Implanted device 208 is configured to facilitate the sampling of low frequency and high frequency electrical signals from electrodes 204. Sampling of brain activity is typically carried out at a rate above about 200 Hz, and preferably between about 200 Hz and about 1000 Hz, and most preferably at or above about 400 Hz. The sampling rates could be higher or lower, depending on the specific features being monitored, patient 202, and other factors. Each sample of the patient's brain activity is typically encoded using between about 8 bits per sample and about 32 bits per sample, and preferably about 16 bits per sample. In alternative embodiments, implanted device 208 may be configured to measure the signals on a non-continuous basis. In such embodiments, signals may be measured periodically or aperiodically.

Patient Advisory Device ("PAD") 214 receives and optionally stores patient data. In one embodiment PAD 214 monitors, in substantially real-time, EEG signals and possibly other physiological signals from implanted device 208. PAD 214 also may be used to record and/or store clinical manifestation data from the patient, such as audio data, heart rate data, accelerometer data, etc. In embodiments where the clinical manifestation data is in the form of audio and/or video recording, the PAD itself may be used to facilitate such monitoring. In other embodiments where the clinical manifestation data is monitored using a separate device such as heart monitor 210 and accelerometer 212, the PAD is generally configured to receive the data monitored by the separate device and can thereafter record and/or store such clinical manifestation data. For example, heart rate data can be monitored by heart monitor 210. The heart rate data can be transmitted to implanted device 208, which can then transmit the heart rate data to PAD 214.

In addition to the physiological signals from implanted unit 208 and the automatic recordings of the audio and/or video data, PAD 214 may also receive and store extracted features, classifier outputs, other patient inputs, and the like. Communication between PAD 214 and implanted device 208 may be carried out through wireless communication, such as a radiofrequency link, infrared link, optical link, ultrasonic link, or other conventional or proprietary wireless link. The wireless communication link between PAD 214 and implanted device 208 may provide a one-way or two-way communication link for transmitting data. Error detection and correction methods may be used to help insure the integrity of transmitted data. If desired, the wireless data signals can be compressed, encrypted, or otherwise processed prior to transmission to PAD 214.

Figure 5:
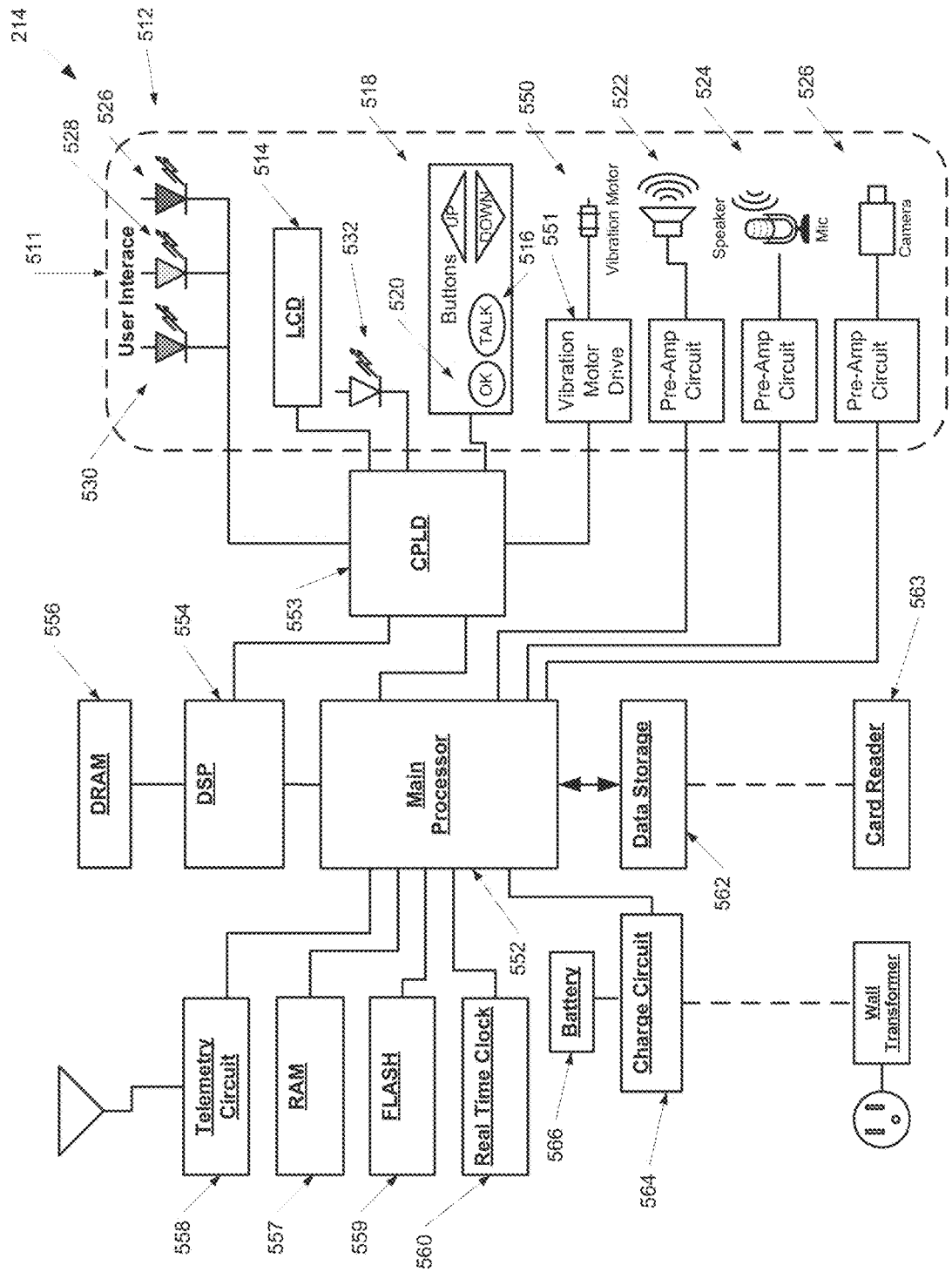
FIG. 5 is a block diagram showing aspects of a monitoring system according to an embodiment of the invention.

In use, electrode arrays 204 are used to sample neurological activity (e.g., EEG signals) from the patient's brain. The sampled brain activity is transmitted from electrode arrays 204 through leads 206 to implanted device 208. In one embodiment implanted device 208 processes (e.g., filters, amplifies, digitizes, compresses, extracts features, and/or encrypts) the sampled brain activity signals and then wirelessly transmits a data signal with patient data to the PAD. As shown in FIG. 5 and described in more detail below, antenna and telemetry circuit 58 in PAD 214 receive the wireless signal from the implanted device with the patient data and transmit the patient data to main processor 552 and/or DSP 554 in the PAD. The patient data may be time stamped and stored in external storage device 562 for subsequent download to a physician computer (not shown). DSP 554 may process the patient data in substantially real-time with one or more brain state algorithms to estimate the patient's brain state, which is described below.

The system components shown in FIG. 2 are intended to be merely exemplary and the system may comprise one or more of those described herein. In addition, any data processing (neurological data or clinical manifestation data) that occurs is not limited to the locations described herein. Data processing may occur in almost any of the system components (e.g., in wireless electrode assemblies, implanted device 208, or an external device such as PAD 214) and it is not limited to the locations in which it is processed as described herein. For example, it may be desirable to perform much of the brain state analysis in implanted device 208 rather than in PAD 214, or it may be desirable to analyze the clinical manifestation data and neurological data in implanted device 208, PAD 214, or other external device such as a physician's workstation.

Figure 3:
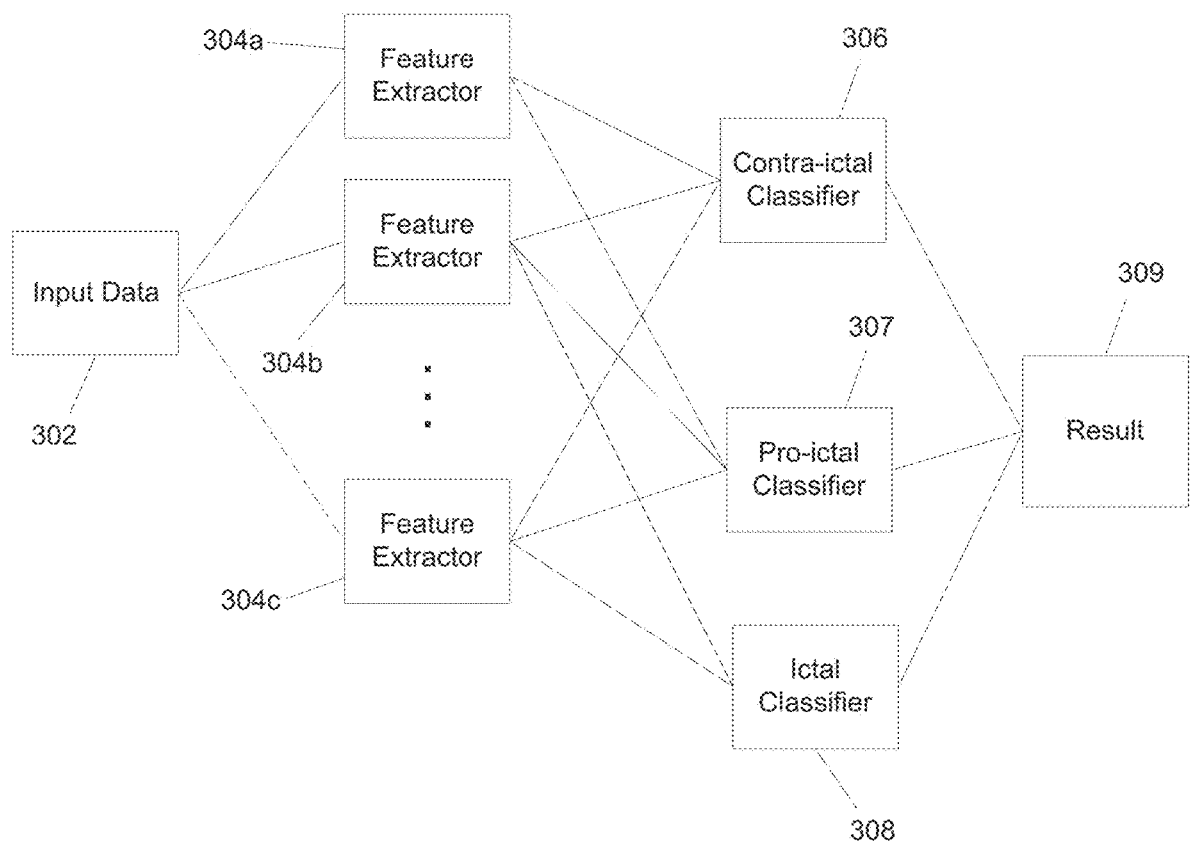
FIG. 3 is a schematic diagram showing aspects of a monitoring system according to an embodiment of the invention.

In one exemplary embodiment of a system according to the instant invention in which the system estimates the patient's propensity for having a seizure, a plurality of brain state algorithms (e.g., safety algorithm, prediction algorithm, and detection algorithm) are optimized or enhanced for different purposes. While each of the algorithms will be optimized for different purposes, the algorithms may use one or more of the same features. For example, as shown in FIG. 3, the PAD (or one of the implanted devices) may comprise a plurality of brain state algorithms which include one or more feature extractors and classifiers. The feature extractors 304a, 304b, 304c are each configured to extract the relevant features from the EEG signals (shown generically in FIG. 3 as "input data 302"). The different brain state algorithms may take the features and use an optimized classifier 306, 307, 308 and attempt to classify the feature vector. For example, the contra-ictal classifier 306 will attempt to determine if the patient is in a brain state in which the patient is highly unlikely to transition into an ictal state within a predetermined time period. The pro-ictal classifier 307 will attempt to determine if the patient is in a pro-ictal brain state in which the patient has an elevated propensity for transitioning into the ictal state. The ictal classifier 308 will attempt to determine if the patient has already transitioned into the ictal state.

Exemplary brain state algorithms which may be used to determine the patient's brain state as described herein are described in U.S. patent application Ser. No. 12/020,450, filed Jan. 25, 2008, and U.S. patent application Ser. No. 12/035,335, filed Feb. 21, 2008, the disclosures of which are incorporated herein by reference. And while the above examples describe three separate algorithms to analyze the patient's brain state, it should be appreciated that a single algorithm may be used to perform the same function of the aforementioned algorithms. Also, there may be more or fewer than three algorithms used to classify the brain state into any number of brain states. The system may also include only one algorithm which is essentially a detection algorithm and could be the equivalent of the ictal classifier to determine if the patient has entered into the ictal state. The system could also only comprise the equivalent of the ictal and pro-ictal classifiers.

In embodiments in which the system provides an output to the patient (e.g., via PAD 214 or similar external device), the outputs of the three different algorithms may be combined in a logical manner to determine the type of output communication that is provided to the patient. FIG. 4 illustrates one example of how the output from three exemplary different brain state algorithms may be used to generate the communication output. In the illustrated embodiment, the output from the algorithms is illustrated as either "0" or "1". A "1" for the safety algorithm would mean that the safety algorithm determined that the patient was "safe" and unlikely to transition into the ictal state within a predetermined time period, whereas a "0" for the safety algorithm means that the patient is not "safe"—but that does not necessarily mean that the patient has an increased propensity for transitioning into the ictal state. A "1" for the prediction algorithm would mean that the prediction algorithm determined that the patient has an elevated propensity for transitioning into the ictal state (e.g., is in a pro-ictal state), whereas a "0" for the prediction algorithm means that the patient does not have an increased propensity for transitioning into the ictal state. A "1" for the detection algorithm would mean that the detection algorithm determined that the patient was in the ictal state, whereas a "0" for the detection algorithm means that the patient is determined to not be in the ictal state.

In the illustrated example of FIG. 4, the possible brain state indicator outputs include a green light (safe brain state), a yellow light (unknown brain state), a blinking red light (pro-ictal brain state), and a flashing red light (ictal brain state). Of course, any type of visual, tactile, and/or audio output could be provided to indicate the patient's brain state, and the present invention is not limited to such outputs.

In the upper left corner of the chart in FIG. 4 is the combination of the outputs from the three algorithms in which the output of all three of the algorithms are "0". In such case, none of the algorithms are able to provide a positive determination and the patient's brain state would fall in the unknown state. Hence, the output to the patient would be the yellow light.

In the bottom left square of the left-most column, where the safety algorithm determines that the patient is safe (safety algorithm output is "1") and neither the prediction algorithm nor the detection algorithm determine that the patient is in a pro-ictal brain state or an ictal brain state (e.g., both are "0"), the patient is deemed to be in a safe brain state and the output to the patient is the green light.

In the middle four boxes—in which the seizure detection algorithm output is a "1", all of the output combinations are determined to be seizure detection and a red flashing light would be provided to the patient with PAD 214. In this configuration, the seizure detection algorithm would take precedent over the seemingly inconsistent results from the safety algorithm and the prediction algorithm. Of course, in other configurations, where the results from the different algorithms are inconsistent, it may be desirable to estimate the patient to be in an "unknown" brain state and provide a yellow light (or similar output that is indicative of the unknown state).

The right column of the chart shows the situation where the seizure prediction algorithm has determined that the patient is in a pro-ictal brain state and the detection algorithm has determined that the patient is not yet in the ictal brain state. In such situations, the output from the prediction algorithm would take precedent over the output from the safety algorithm and the output to the patient would be that of "seizure predicted" and a red flashing light would be provided. In other configurations, in the situation where the safety algorithm is inconsistent with the prediction algorithm (e.g., both are "1"), it may be desirable to estimate the patient to be in an "unknown" brain state and provide a yellow light (or similar output).

Thus, depending on the output(s) from the brain state algorithms, the appropriate brain state indicator is illuminated on PAD and/or an audible or tactile alert is provided to the patient when the patient's brain state changes. The PAD may also include an "alert" or "information" indicator (such as an LED, or tone) that alerts the patient that a change in brain state or system component state has occurred, or that user intervention is required. This alert indicator may occur in conjunction with another alert, and may simply be used as a universal indicator to the patient that the user needs to pay attention to the PAD and/or intervene.

The brain state indicators on PAD 214 allow the patient to substantially continuously monitor the brain state on a real-time basis. Such brain state indicators may be used by the patient to assess which activities "trigger" their brain to move them from a "safe" state to an "unknown" or "pro-ictal state." Consequently, over time the patient may be able to avoid the particular triggers.

FIG. 5 shows a simplified block diagram of an exemplary embodiment of a PAD which is part of a system designed to receive a patient's neurological data and receive and/or monitor clinical manifestation data. As noted above, the patient's neurological data may be processed to determine the patient's propensity for having a seizure while the clinical manifestation data may be used subsequently to confirm the occurrence of the seizure (or determine that a seizure did not occur), and such data may thereafter be used to adjust one or more parameters of the system.

The illustrated PAD shows a user interface 511 that includes a variety of indicators for providing system status and alerts to the patient. User interface 511 may include one or more indicators 512 that indicate the patient's brain state. In the illustrated embodiment, the output includes light indicators 512 (for example, LEDs) that comprise one or more discrete outputs that differentiate between a variety of different brain states. In the illustrated embodiment, the brain state indicators 512 include a red light 526, yellow/blue light 528, and a green light 530 for indicating the patient's different brain states. In some configurations the lights may be solid, blink or provide different sequences of flashing to indicate different brain states. If desired, the light indicators may also include an "alert" or "information" light 532 that is separate from the brain state indicators so as to minimize the potential confusion by the patient. In other embodiments the PAD is part of a system that is merely a detection system, or part of a system that can indicate detection and an increased likelihood of having a seizure (pro-ictal), but does not necessarily determine when the patient is in a contra-ictal brain state. In other embodiments, the system may only be used for a "safety monitor" and may only indicate when the patient is in the contra-ictal brain state. Exemplary methods and systems for providing alerts to the patient can be found in a commonly owned U.S. patent application filed concurrently with this application entitled "Patient Advisory EEG Analysis Method and Apparatus", the disclosure of which is incorporated herein by reference.

Figure 6:
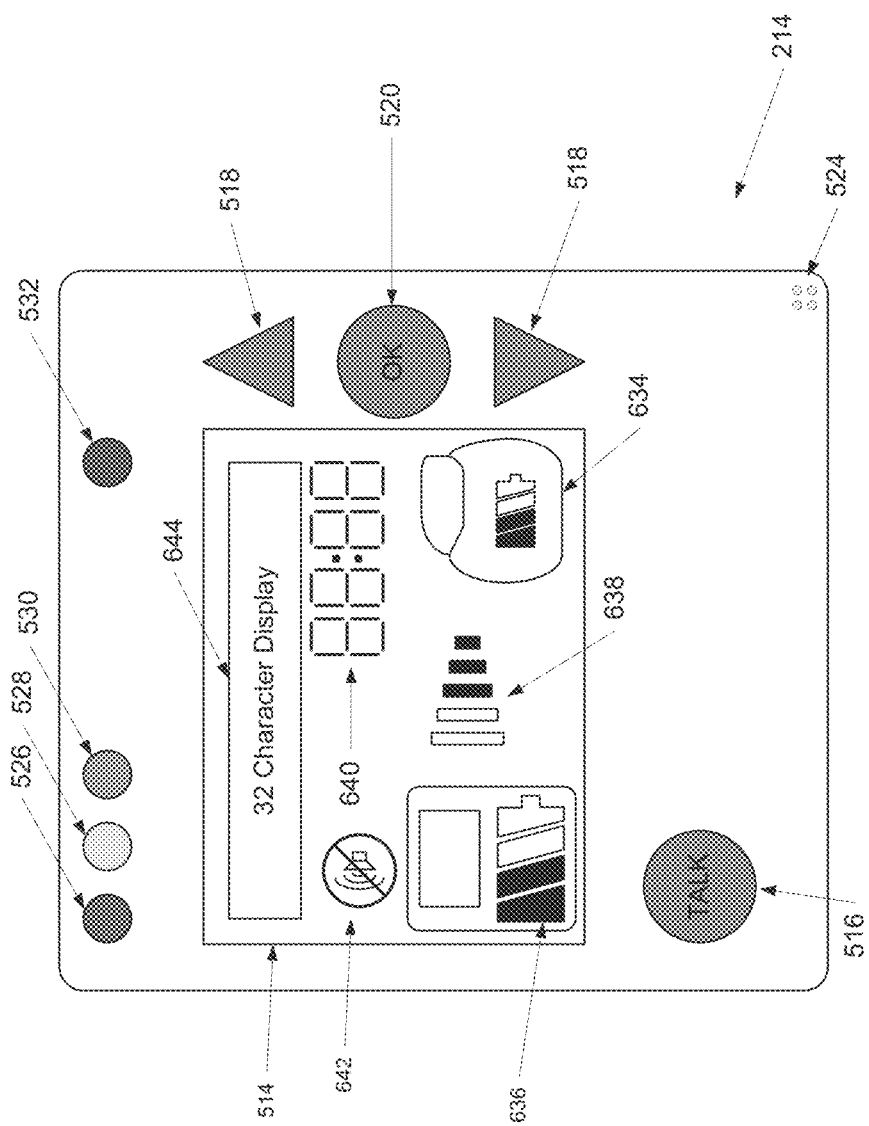
FIG. 6 shows aspects of a display for a monitoring system according to an embodiment of the invention.

PAD 214 may also include a liquid crystal display ("LCD") 514 (which can be seen in more detail in FIG. 6) or other display for providing system status outputs to the patient. The LCD 514 generally displays the system components' status and prompts for the patient. For example, as shown in FIG. 6, LCD 514 can display indicators, in the form of text or icons, such as, for example, implantable device battery strength 634, PAD battery strength 636, and signal strength 638 between the implantable device and the PAD. If desired, the LCD may also display the algorithm output (e.g., brain state indication) and the user interface 511 may not require the separate brain state indicator(s) on other portions of the PAD. The output on the LCD can be continuous, but in some embodiments may appear only upon the occurrence of an event or change of the system status and/or the LCD may enter a sleep mode until the patient activates a user input. LCD 514 is also shown including clock 640, audio status 642 (icon shows PAD is muted), and character display 644 for visual text alerts to the patient—such as an estimated time to seizure or an estimated "safe" time. While not shown in FIG. 6, LCD 514 may also indicate the amount of free memory remaining on the memory card.

Referring again to FIG. 5, PAD 214 may also include speaker 522 and a pre-amp circuit to provide audio outputs to the patient (e.g., beeps, tones, music, recorded voice alerts, etc.) that may indicate brain state, change in brain state, or system status outputs to the patient. User interface 511 may also include a vibratory output device 550 and vibration motor drive 551 to provide a unique tactile alert to the patient that indicates a specific brain state, which may be used separately from or in conjunction with the visual and audio outputs provided to the patient. Depending on the desired configuration any of the aforementioned outputs may be combined to provide information to the patient.

PAD 214 typically comprises at least one input device that allows the PAD to monitor and/or record clinical manifestation data which is indicative of the occurrence of a clinical seizure. The input device can be automatically activated, user-activated, or a combination thereof. PAD 214 may include a circular buffer in RAM 557 to buffer the clinical manifestation data. If a seizure is detected and/or predicted, the clinical manifestation data may then be written and permanently stored in data storage 562. While SRAM is one preferred embodiment of the type of memory for storing the clinical manifestation data files, other types of conventional types of memory (e.g., FLASH 559) may also be used.

Inputs include, for example, one or more physical inputs (e.g., buttons 516, 518, 520) that may be used to activate an audio input (in the form of a microphone 524 and a pre-amp circuit) and/or a video input (in the form of a video capture device 526 and a pre-amp circuit). In some uses, the inputs can be used by the patient to make time-stamped notes or annotations that may be overlaid on the patient's EEG data file. Such notes could include, occurrence of a clinical seizure (e.g., clinical manifestation data), feeling of an aura (a different feeling, smell, taste, etc.), taking of an anti-epileptic drug, indication of sleep state ("I'm going to sleep," "I just woke up," "I'm tired," etc.) Such notes or annotations may be stored in a separate data file or as part of the patient's EEG or brain state files.

For example, in some embodiments the PAD comprises a dedicated user activated input button that allows the user to simply depress the input button to indicate that that the patient is experiencing a clinical manifestation of a seizure or an aura. Upon user-activation a separate clinical manifestation data file can be created, receive a date and time-stamp, and can be stored on the PAD and/or transmitted in substantially real-time to another device, such as a physician's computer system over a wireless network. Alternatively, the neurological data (e.g., EEG data) which is being processed by the system can simply be automatically annotated with the date and time and type of input (e.g., "user-activated aura indicator," or "automatic convulsion indicator"). If the clinical manifestation information is saved as a separate data file, it can be subsequently analyzed with the neurological data to determine if one of the clinical manifestation data and the neurological data indicate the occurrence of a seizure while the other does not. If this is the case, the system, such as an algorithm in the system, can be re-trained to improve the accuracy of the system in predicting and/or detecting seizures. This process is described in more detail below.

In some embodiments, a user-activated input may be configured to allow the patient to record any type of audio, such as voice data using the microphone. As shown in FIG. 5, a dedicated voice recording user input 516 may be activated to allow for voice recording. In preferred embodiments, the voice recording may be used as an audio patient seizure diary. Such a diary may be used by the patient to record when a seizure has occurred, when an aura or prodrome has occurred, when a medication has been taken, to record patient's sleep state, stress level, etc. Such voice recordings may be time stamped and stored in data storage of the PAD and may be transferred along with recorded EEG signals to the physician's computer. Such voice recordings may thereafter be overlaid over the EEG signals and used to interpret the patient's EEG signals and improve the training of the patient's customized algorithm(s), if desired.

Such user activated inputs may thereafter be compared to the outputs of the brain state algorithms to assess a number of different things. For example, the number of seizures detected by the detection algorithm may be compared to the number of auras that the patient experienced. Additionally, the number of seizures detected by the detection algorithm may be compared to the patient's seizure log to assess how many of the seizures the patient was able to log. In other aspects, the physician may ask that the patient make a notation in the log every time an anti-epileptic drug is taken. Such a log could be used to monitor the patient's compliance, as we as to determine the effect of the anti-epileptic drug on the patient's EEG.

In other embodiments, the PAD (or other device within the system) may be adapted to include automatic inputs for automatically monitoring and/or recording clinical manifestation data which is indicative of the occurrence of a seizure. Exemplary automatic inputs include a microphone and preamp circuit (which can automatically monitor and/or record audio data from the patient such as an ictal-moan), a convulsion detector (e.g., accelerometer which can automatically monitor and/or record a patient's rhythmic movement or jerking that is indicative of the patient's clinical seizure), a heart rate monitor (which can automatically monitor and/or record a patient's heart rate or the like), and/or a video recording unit (similar to those in cellular phones) which can automatically record video of the patient.

The different inputs can be disposed within the PAD, a separate device external to the patient, or they may be disposed within or on the patient. If the input device is disposed in the PAD, the PAD can monitor the clinical manifestation data and either store the data in the PAD or transmit it to a separate external device such as a physician's computer. If the input device is disposed within or on the patient, or in a separate external device, the monitored clinical manifestation data, processed or unprocessed, can be transmitted to the PAD, where it can be stored or further transmitted to a separate external device such as a physician's computer. As described above, the devices used to automatically monitor and/or record the clinical manifestation data can be disposed in any of the system components described herein, and the data can be processed and/or stored in any of the system components described herein. For example, a microphone can be disposed within the PAD to monitor and record audio data while a heart rate monitor can be disposed on or within the patient to monitor the patient's heart rate.

In an exemplary embodiment, a convulsion detector, such as an accelerometer, can be built into the PAD or other external device worn or held by the patient, or it can be disposed internally within the patient, such as in the implanted device 208 or implanted elsewhere in the patient's body as illustrated as detector 212 in FIG. 2. The convulsion detector is shown in communication with implanted device 208, which is in communication with PAD 214, via conventional wired and wireless communication links. The convulsion detector (wherever it may be disposed) can detect a convulsion associated with a seizure and transmit a data signal to the PAD that a convulsion/seizure has occurred. The PAD may then automatically date and time-stamp the convulsion occurrence, which can then be annotated on the EEG data or which can then be stored as a separate data file. Again, the occurrence of this clinical manifestation of the occurrence of a seizure can then be compared to the stored EEG data, or the brain state estimation, for training purposes.

In a second example of automatically recording clinical manifestation data, as shown schematically in FIG. 2 the heart rate monitor 210 may be in communication with the implanted device 208 or PAD 214 via conventional wired or wireless communication links. Heart rate monitor 210 may be used to monitor a change in heart rate (e.g., autonomic tone via R-R interval variability) that is indicative of a seizure and transmits a data signal to the PAD that a change in heart rate that is indicative of seizure has occurred. The PAD may then automatically date and time-stamp the occurrence, which can then be annotated on the EEG data or which can then be stored as a separate data file. Again, the occurrence of this clinical manifestation of the occurrence of a seizure can then be compared to the stored EEG data, or the brain state estimation, for training purposes.

In a third example of automatically recording clinical manifestation data, the automatic input device is a microphone on the PAD and is automatically activated to record audio data from the patient. This can be used to record audio clinical manifestations of a seizure, such as, for example, a so-called "ictal moan" or "ictal gasp" that may be caused by tonic contraction of muscles. This is a distinguishable sound to a practiced clinician and can be discerned by listening to the recorded audio data. In some configurations, it may be desirable to use speech recognition software to automatically determine if there is an audio recording of the clinical manifestation of the patient's seizure. Such speech recognition software would be made patient specific by training on the patient's previous occurrence of a seizure.

In this third example (but may be applied to any of the embodiments described herein), the microphone may be configured to automatically continuously record audio data in a first-in first-out (FIFO) manner where the current audio data over-writes the oldest data as memory storage capacity is exceeded. In the event that the system determines that a neurological event has occurred or the patient's brain state has changed (e.g., the system determined that a seizure has been detected or predicted, the patient has changed from a safe-state to a pro-ictal state, the system has predicted the onset of a seizure, etc.), the PAD automatically begins to permanently store the monitored audio data for a specific period of time preceding (e.g., the "pre-trigger timer period" anywhere from a few seconds (10 seconds to 5 minutes) and/or following the trigger ("post trigger") while continuing to monitor and store the patient's EEG information. If an audio clinical manifestation has occurred, it will be recorded via the microphone and stored in memory. As described above, the monitored EEG data or determined brain state can then be annotated with the indication of the occurrence (including date/time stamp) of the clinical manifestation of the seizure (e.g., "ictal moan automatically recorded"), or the clinical manifestation data can be stored as a separate file, date and time-stamped, and stored in the PAD memory or transmitted to another device. It can then be compared to the EEG data or brain state.

In an alternative embodiment in which the clinical manifestation data is automatically monitored and/or recorded, the clinical manifestation data is not continuously monitored and recorded. Rather, the PAD or other device may automatically initiate audio monitoring and/or recording upon the occurrence of an event in the patient's condition or upon the occurrence of a change in the patient's brain state. Examples of events that can trigger the automatic monitoring and/or recoding of clinical manifestation data include, without limitation, when the system detects a seizure, when the system detects a change from a safe-state to pro-ictal state, the system predicts the onset of a seizure, the system detects an increased likelihood of having a seizure, etc.). The data can be time-stamped and used for training or retraining purposes as described above. To avoid missing the recordation of a clinical manifestation, it would likely be beneficial for the PAD to initiate recording as soon as the system detects an event. For example, the PAD can start recording the clinical manifestation data when the system estimates a change from a safe-state to a pro-ictal state or when the onset of a seizure is predicted.

In some configurations, the PAD is adapted to automatically switch from a first mode (where clinical manifestation data is continuously recorded) to a second mode in which the clinical manifestation data is recorded only upon the occurrence of a change in the patient's condition. This can be advantageous if the remaining storage in the device falls below a certain threshold. In other embodiments, the PAD may always be set in the second mode.

In a fourth example of the automatic input device the video recording unit 526 (the video recording unit may alternatively be disposed in a device other than the PAD) may be configured to continuously record video data in a first-in first-out (FIFO) manner where the current video data over-writes the oldest data as memory storage capacity is exceeded, in a manner similar to that described above for the automatic audio recording. In an alternative embodiment of automatic video recording, the video data may not always be continuously monitored and recorded, rather, the video data may be automatically initiated upon the occurrence of an event, as described above (e.g., the system detects a seizure, a change from safe-state to pro-ictal state, the system predicts the onset of a seizure, etc.).

While it has been previously proposed to use accelerometer data and video data to detect an onset of a clinical seizure in a hospital setting, such data has not been collected with an ambulatory device and such data does not appear to be used to confirm the electrographic onset of a seizure for assessing performance and possible retraining of a seizure monitoring system. One exemplary advantage of an ambulatory system with such capabilities is that a seizure detection system can be retrained and yet the patient does not have to be confined to a hospital or other non-ambulatory setting.

Recording the clinical manifestation data can also assist in the classification of the monitored electrographic seizure activity as either sub-clinical (not manifesting clinically) or clinical (associated with a clinical manifestation), which is described in more detail below.

While the above describes preferred physiological and non-physiological data that may be used to confirm the clinical onset of a seizure, there are other types of clinical manifestation data that may be used. For example, it may be possible to monitor the patient's respiration via impedance pneumograph, a skin temperature, electrical impulses of muscles via electromyography (EMG) sensors, or the like.

Referring again to FIG. 5, similar to conventional cellular phones, inputs 516, 518, 520 may be used to toggle between the different types of outputs provided by the PAD. For example, the patient can use buttons 516, 518 to choose to be notified by tactile alerts such as vibration rather than audio alerts (if, for example, a patient is in a movie theater). Or the patient may wish to turn the alerts off altogether (if, for example, the patient is going to sleep). In addition to choosing the type of alert, the patient can choose the characteristics of the type of alert. For example, the patient can set the audio tone alerts to a low volume, medium volume, or to a high volume.

The one or more inputs may also be used to acknowledge system status alerts and/or brain state alerts. For example, if PAD 214 provides an output that indicates a change in brain state, one or more of the LEDs 512 may blink, the vibratory output may be produced, and/or an audio alert may be generated. In order to turn off the audio alert, turn off the vibratory alert and/or to stop the LEDs from blinking, the patient may be required to acknowledge receiving the alert by actuating one of the user inputs (e.g., acknowledge/okay button 520).

While the PAD is shown having inputs 516, 518, 520, any number of inputs may be provided on PAD. For example, in one alternate embodiment, the PAD may comprise only two input buttons. The first input button may be a universal button that may be used to scroll through output mode options. A second input button may be dedicated to voice recording. When an alert is generated by the PAD, either of the two buttons may be used to acknowledge and deactivate the alert. In other embodiments, however, there may be a dedicated user input for acknowledging the alerts.

PAD 214 may comprise main processor 552 and complex programmable logic device (CPLD) 553 that control much of the functionality of the PAD. In the illustrated configuration, main processor and/or CPLD 553 control the outputs displayed on LCD 514, generates the control signals delivered to vibration device 550 and speaker 522, and receives and processes the signals from buttons 516, 518, 520, microphone 524, video assembly 526, and real-time clock 560. Real-time clock 560 may generate the timing signals that are used with the various components of the system.

The main processor may also manage data storage device 562 and manage telemetry circuit 558 and charge circuit 564 for a power source, such as battery 566.

While main processor 552 is illustrated as a single processor, the main processor may comprise a plurality of separate microprocessors, application specific integrated circuits (ASIC), or the like. Furthermore, one or more of microprocessors 552 may include multiple cores for concurrently processing a plurality of data streams.

CPLD 553 may act as a watchdog to main processor 552 and DSP 554 and may flash LCD 514 and brain state indicators 512 if an error is detected in DSP 554 or main processor 552. Finally, CPLD 553 controls the reset lines for main microprocessor 552 and DSP 554.

Telemetry circuit 558 and antenna may be disposed in PAD 214 to facilitate one-way or two-way data communication with the implanted device. Telemetry circuit 558 may be an off the shelf circuit or a custom manufactured circuit. Data signals received from the implanted device by telemetry circuit 558 may thereafter be transmitted to at least one of DSP 554 and main processor 552 for further processing.

DSP 554 and DRAM 556 receive the incoming data stream from main processor 552. In embodiments in which the PAD comprises the brain state algorithms, the brain state algorithms process the data (for example, EEG data) and estimate the patient's brain state, and can be executed by DSP 554 in the PAD. In other embodiments, however, the brain state algorithms may be implemented in the implanted device, and the DSP may be used to generate the communication to the patient based on the data signal from the algorithms in the implanted device. The algorithms can also be stored in a device remote from the patient, such as a physician's computer system. The implanted device and the PAD could primarily transmit the monitored data to the remote device for subsequent processing.

Main processor 552 is also in communication with data storage device 562. Data storage device 562 preferably has at least about 7 GB of memory so as to be able to store data from about 16 channels at a sampling rate of between about 200 Hz and about 1000 Hz. With such parameters, it is estimated that the 7 GB of memory will be able to store at least about 1 week of patient data. Of course, as the parameters (e.g., number of channels, sampling rate, etc.) of the data monitoring change, so will the length of recording that may be achieved by the data storage device 562. Furthermore, as memory capacity increases, it is contemplated that the data storage device will be larger (e.g., 10 GB or more, 20 GB or more, 50 GB or more, 100 GB or more, etc.). Examples of some useful types of data storage device include a removable secure digital card or a USB flash key, preferably with a secure data format. The storage device can be used to store raw neurological data (e.g., EEG data), processed neurological data (e.g., determined brain states), clinical manifestation data, raw or processed neurological data annotated with the occurrence of the clinical manifestation of a seizure, etc.

"Patient data" as used herein may include one or more of raw analog or digital EEG signals, compressed and/or encrypted EEG signals or other physiological signals, extracted features from the signals, classification outputs from the algorithms, monitored clinical manifestation data, etc. Data storage device 562 can be removed when full and read in card reader 563 associated with the patient's computer and/or the physician's computer. If the data card is full, (1) the subsequent data may overwrite the earliest stored data as described above, or (2) the subsequent data may be processed by DSP 554 to estimate the patient's brain state (but not stored on the data card). While preferred embodiments of data storage device 562 are removable, other embodiments of the data storage device may comprise a non-removable memory, such as FLASH memory, a hard drive, a microdrive, or other conventional or proprietary memory technology. Data retrieval off of such data storage devices 562 may be carried out through conventional wired or wireless transfer methods.

The power source used by PAD 214 may comprise any type of conventional or proprietary power source, such as a non-rechargeable or rechargeable battery 566. If a rechargeable battery is used, the battery is typically a medical grade battery of chemistries such as a lithium polymer (LiPo), lithium ion (Li-Ion), or the like. Rechargeable battery 566 will be used to provide the power to the various components of PAD 214 through a power bus (not shown). Main processor 552 may be configured to control charge circuit 564 that controls recharging of battery 566.

In addition to being able to communicate with an implanted device, the PAD may have the ability to communicate wirelessly with a remote device—such as a server, database, physician's computer, manufacturer's computer, or a caregiver advisory device (all interchangeably referred to herein as "CAD"). In the exemplary embodiment, the PAD may comprise an additional communication assembly (not shown) in communication with main processor 552 that facilitates the wireless communication with the CAD. The communication assembly may be a conventional component that is able to access a wireless cellular network, pager network, wifi network, or the like, so as to be able to communicate with the remote device. Any of the information stored in PAD 214 may be transmitted to the remote device.

In some embodiments, PAD 214 is able to deliver a signal through the communication assembly that is received by a remote device, in either real-time or non-real-time. Real-time transfer of data could include the real-time transfer of the patient's brain state, clinical manifestation data, patient notes (e.g., seizure log, etc.) so as to inform a caregiver of the occurrence of a seizure or the patient's brain state or change in brain state, as determined by the PAD. The CAD would allow the caregiver to be away from the patient (and give the patient independence), while still allowing the caregiver to monitor the occurrence of clinical manifestation data, seizures, the patient's brain state, and the patient's propensity for seizure. Thus, if the patient's brain state indicates a high propensity for a seizure or the occurrence of a seizure, the caregiver would be notified via the CAD, and the caregiver could facilitate an appropriate treatment to the patient (e.g., small dosage of an antiepileptic drug, make the patient safe, etc.).

In other embodiments, the communication assembly could be used to facilitate either real-time or non-real time data transfer to the remote server or database. If there is real time transfer of data, such a configuration could allow for remote monitoring of the patient's brain state, recorded EEG data, and/or clinical manifestation data. Non-real time transfer of data could expedite transfer and analysis of the patient's recorded EEG data, clinical manifestation data, extracted features, or the like. Thus, instead of waiting to upload the brain activity data from the patient's data storage device, when the patient visits their physician, the physician may have already had the opportunity to review and analyze the patient's transferred brain activity data and clinical manifestation data prior to the patient's visit.

Some embodiments include a system which can be toggled between two or more different modes of operation. In one example, a first mode of operation of the PAD (or other device) may be primarily data collection and algorithm training, in which the monitored neurological signals (e.g., EEG signals), brain state estimations, and clinical manifestation data are transmitted or transferred to a remote device (e.g., to the physician). It may be desirable to also run a generalized (i.e., not patient-specific) seizure detection algorithm in conjunction with the automatic clinical manifestation recording means (e.g., record audio, video, heart rate, movement). It can then be determined if there is an association between a clinical manifestation of a seizure and the neurological signals and/or brain state estimations. It should be noted that in some embodiments the clinical manifestation data can be compared to the raw EEG data, while in other embodiments the clinical manifestation data can be compared with the determined brain states or the extracted features (or compared to all of the different data).

In a second mode of operation, after the brain state algorithms have been trained (either using the monitored clinical manifestation data and neurological data that was collected during the first mode of operation, or simply by using collected neurological data), the brain state algorithms may be implemented to process substantially real-time data signals to determine the patient's brain state. The brain state indicators may also be enabled to inform the patient of their substantially real-time brain state status. The system can, however, continue to automatically record the clinical manifestation data upon the occurrence of a change in the patient's condition. The recorded clinical manifestation data can then be compared to the neurological data or determined brain state to determine if the system is accurately predicting seizure activity. The system can then be retrained as necessary. This process can occur as frequently as desired. In fact, system can be set up to automatically record clinical manifestation data for the life of the system.

In a third mode of operation, it may be desirable to only receive and process the data signals from the implanted device and the PAD, but no longer store the monitored data signals in a memory of the PAD. For example, if the brain state algorithms are performing as desired, the brain data signals and the clinical manifestation data will not have to be stored and analyzed. Consequently, the patient would not have to periodically replace the data card in the PAD as frequently. However, it may still be desirable to store clinical manifestation data and/or neurological data signals that immediately precede and follow any detected seizure. Consequently, in the third mode such seizure data signals may optionally be stored.

As noted above, the PAD will typically comprise one or more brain state algorithms. In one embodiment, the brain state algorithms will generally characterize the patient's brain state as either "Safe or Low Propensity," "Unknown," "Prediction or Elevated Propensity" or "Detection." It is intended that these are meant to be exemplary categories only and are in no way to be limiting and additional brain states or fewer brain state indicators may be provided. There may be different types of algorithms which are configured to characterize the brain state into more or less discrete states. "Safe" generally means that brain activity indicates that the patient is in a contra-ictal state and has a low susceptibility to transition to an ictal state for an upcoming period of time (for example, 60 minutes to 90 minutes). This is considered positive information and no user lifestyle action is required. A "prediction" state generally means that the algorithm(s) in the PAD are determining that the patient is in a pro-ictal state and has an elevated propensity for a seizure (possibly within a specified time period). A "detection" state generally means that brain activity indicates that the patient has already transitioned into an ictal state (e.g., occurrence of an electrographic seizure) or that there is an imminent clinical seizure. User actions should be focused on safety and comfort. An "unknown" state generally means the current type of brain activity being monitored does not fit within the known boundaries of the algorithms and/or that the brain activity does not fit within the contra-ictal state, pro-ictal state, or ictal state. Therefore no evaluation can be reliably made. "Unknown" can also indicate there has been a change in the status of the brain activity and while the patient does not have an elevated propensity and no seizure has been detected, it is not possible to reliable tell the patient they are substantially safe from transitioning into an ictal state for a period of time. This state is considered cautionary and requires some cautionary action such as limiting exposure to risk. The two different types of "unknown" may have separate brain state indicators, or they may be combined into a single brain state indicator, or the user interface may not provide the "unknown" state to the patient at all.

In one method, the physician (or software, as the training can be partially automated) first determines if a clinical manifestation of a seizure occurred by investigating or analyzing the clinical manifestation data (e.g., ictal moan in an audio file, a convulsion indication from a convulsion detection file, a change in heart rate from the heart monitor file, video indication from a video file, etc.). As discussed above, in some embodiments the clinical manifestation data is stored in a separate data file, while is some embodiments the monitored EEG data or a recordation of the determined brain state is annotated with an indication of the occurrence of a clinical manifestation of a seizure. Either way, the physician can determine when the clinical manifestation occurred. The physician can then analyze the estimated brain state output from the algorithm(s) before and after the occurrence of the documented clinical manifestation. The physician can then determine if the system accurately estimated the brain state before and/or during the seizure. For example, if the physician observes a recorded ictal moan, preferably the system had estimated a pro-ictal state for a period of time before the ictal moan. In addition, the system would have preferably estimated an ictal state at or near in time to the occurrence of the ictal moan.

If the system did not detect either a pro-ictal state or an ictal state (or predict a seizure), the algorithm(s) may need to be reprogrammed/re-trained using the patient's EEG data before and near the point in time the clinical manifestation was detected. This technique can also be used in an initial step in programming of the system to train the algorithms for patient-specific prediction and/or detection. In a system designed simply to predict the onset of a seizure or to detect the onset of a seizure, the clinical manifestation data can similarly be used to determine if the system correctly determined if a seizure occurred or predicted the onset of the seizure.

In a second method, the physician (or software) may first determine when the system determined a neurological event occurred (e.g., a detected seizure, an increased likelihood of having a seizure, a change in brain state, etc.), and then looks for clinical manifestation data that was recorded near in time to the event to determine if there was any recorded clinical manifestation associated with the estimated neurological activity. Similar to the above method, the algorithms can then be retrained as necessary to improve their accuracy.

In this second method, an absence of clinical manifestation data does not necessarily mean the algorithm(s) which detected or predicted a seizure was incorrect, as there may not have been, for example, an ictal moan associated with the clinical seizure that in fact occurred. Alternatively, a convulsion may not have been forceful enough to trigger the convulsion detector. Or, in some situations, the patient may have had an electrographic seizure with no clinical manifestation (i.e., sub-clinical). However, in such situations the physician might consider the alert a false positive, and determining an absence of a clinical manifestation of a seizure can assist in the determination of false positives and such information may thereafter be used in metrics for assessing the specificity and sensitivity of the algorithm, which may later lead to retraining of the algorithm(s) to reduce the occurrence of such false positives. Exemplary methods and systems that can be used in the comparing and/or analyzing steps described herein can be found in a commonly owned U.S. patent application filed concurrently with this application entitled "Patient Advisory EEG Analysis Method and Apparatus", the disclosure of which is incorporated herein by reference.

A lack of detected clinical manifestation data could, however, also necessitate an adjustment of the parameters used to monitor and record clinical manifestations of the occurrence of a seizure. For example, the audio recording sensitivity may need to be increased to record very soft audio data which is indicative of the occurrence of a seizure. Or the convulsion detector (e.g., accelerometer positioned somewhere in or on the patient) may need to be adjusted to a more sensitive setting. Adjusting the sensitivity and parameters used to automatically monitor and record clinical manifestation data may therefore be required after analyzing the clinical manifestation data with the neurological data or the patient's brain state.

Additional features which can be incorporated in a PAD or other system device as described herein are described in co-pending U.S. patent application Ser. No. 12/180,996, filed Jul. 28, 2008, the entire disclosure of which is incorporated by reference herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method of detecting a neurological status of a subject, the method comprising:
   extracting, by a processor, a first set of features from a neurological signal acquired from the subject;
   performing, by the processor, a first determination of a neurological state of the subject by classifying the first set of features based on predefined neurological states;
   recording an accelerometer signal, via an accelerometer, from the subject contemporaneously with the neurological signal;
   extracting from the accelerometer signal, by the processor, clinical manifestation data indicative of at least one of rhythmic movement or jerking indicative of convulsions of the subject;
   extracting, by the processor, a second set of features from the accelerometer signal;
   performing, by the processor, a second determination of the neurological state of the subject by classifying the second set of features, wherein the second set of features is classified based on the predefined neurological states and at least one parameter;
   comparing, by the processor, the first and second determinations;
   identifying, by the processor, a brain state of the subject based on the comparison;
   selecting an indication from among a plurality of indications, the plurality of indications including a first indication corresponding to a safe brain state, a second indication corresponding to an unknown brain state, and a third indication corresponding to an ictal brain state, and wherein the selected indication corresponds to the identified brain state; and
   providing the selected indication of the identified brain state.

2. The method of claim 1, wherein the neurological signal is at least one of an EEG signal and an ECoG signal.

3. The method of claim 1, wherein the first and second determinations are inconsistent with each other.

4. The method of claim 3, wherein the first determination indicates that the subject is not experiencing a seizure and the second determination indicates that the subject is experiencing a seizure.

5. The method of claim 3, wherein the first determination indicates that the subject is experiencing a seizure and the second determination indicates that the subject is not experiencing a seizure.

6. The method of claim 1, wherein one of the first and second determinations does not indicate an occurrence of a seizure.

7. The method of claim 1, wherein the comparing of the first and second determinations includes identifying a deficiency in at least one of the first and second determinations.

8. A method of monitoring a seizure status of a subject, the method comprising:
   monitoring, by a neurological sensor and an accelerometer, the subject;
   detecting a first seizure state indicator by extracting a first set of features from a neurological signal obtained from the neurological sensor monitoring the subject and classifying the first set of features based on predefined neurological states;
   contemporaneously recording an accelerometer signal, via the accelerometer, from the subject;
   detecting a second seizure state indicator by extracting a second set of features from clinical manifestation data obtained from the accelerometer signal monitoring the subject and classifying the second set of features, wherein the second set of features are classified based on the predefined neurological states, the clinical manifestation data indicating at least one of rhythmic movement or jerking indicative of convulsions of the subject, and at least one parameter;
   comparing the detected first seizure state indicator to the detected second seizure state indicator, wherein the detected first seizure state indicator is detected using the first set of features and the detected second seizure state is detected using the second set of features;
   identifying a brain state of the subject based on the comparison;
   selecting an indication from among a plurality of indications, the plurality of indications including a first indication corresponding to a safe brain state, a second indication corresponding to an unknown brain state, and a third indication corresponding to an ictal brain state, and wherein the selected indication corresponds to the identified brain state; and
   providing the selected indication of the identified brain state.

9. The method of claim 8, wherein the neurological sensor is disposed to monitor the subject's brain, and wherein the neurological signal is at least one of an EEG signal and an ECoG signal.

10. The method of claim 8, wherein the first seizure state indicator and the second seizure state indicator are consistent with each other.

11. The method of claim 8, wherein the first seizure state indicator and the second seizure state indicator are inconsistent with each other.

12. The method of claim 11, wherein the first seizure state indicator indicates a non-ictal state of the subject and the second seizure state indicator indicates an ictal state of the subject.

13. The method of claim 11, wherein the first seizure state indicator indicates an ictal state of the subject and the second seizure state indicator indicates a non-ictal state of the subject.

14. The method of claim 8, wherein one of the first seizure state indicator and the second seizure state indicator does not indicate a brain state of the subject.

15. The method of claim 8, wherein the comparing of the detected first seizure state indicator using the first set of features and the detected second seizure state indicator using the second set of features includes identifying a deficiency in at least one of the detection of the first seizure state indicator and the detection of the second seizure state indicator.

16. A method of monitoring a neurological status of a subject, the method comprising:
   acquiring a neurological signal from the subject;
   extracting, by a processor, a first set of features from the neurological signal;
   identifying, by the processor, a first indicator by classifying the first set of features based on predefined neurological states, the first indicator associated with a first characterization of a brain state of the subject;
   recording an accelerometer signal, via an accelerometer, from the subject contemporaneously with the neurological signal;

extracting from the accelerometer signal, by the processor, clinical manifestation data indicative of at least one of rhythmic movement or jerking indicative of convulsions of the subject;

extracting, by the processor, a second set of features from the accelerometer signal;

identifying, by the processor, a second indicator by classifying the second set of features, wherein the second set of features are classified based on the predefined neurological states and at least one parameter, the second indicator associated with a second characterization of the brain state of the subject;

comparing, by the processor, the first characterization of the brain state of the subject to the second characterization of the brain state of the subject;

identifying, by the processor, the brain state of the subject based on the comparison;

selecting an indication from among a plurality of indications, the plurality of indications including a first indication corresponding to a safe brain state, a second indication corresponding to an unknown brain state, and a third indication corresponding to an ictal brain state, and wherein the selected indication corresponds to the identified brain state; and providing the selected indication of the identified brain state.

17. The method of claim 16, wherein the neurological signal is at least one of an EEG signal and an ECoG signal.

* * * * *